United States Patent
Otake

(10) Patent No.: US 7,172,728 B2
(45) Date of Patent: *Feb. 6, 2007

(54) TEST STRIP CONTAINERS AND METHODS OF USING THE SAME

(75) Inventor: Gary Otake, Union City, CA (US)

(73) Assignee: LifeScan, Inc., Milpitas, CA (US)

( * ) Notice: Subject to any disclaimer, the term of this patent is extended or adjusted under 35 U.S.C. 154(b) by 473 days.

This patent is subject to a terminal disclaimer.

(21) Appl. No.: 10/116,086

(22) Filed: Apr. 2, 2002

(65) Prior Publication Data

US 2003/0185708 A1    Oct. 2, 2003

(51) Int. Cl.
 *G01N 31/22* (2006.01)
 *G01N 21/00* (2006.01)

(52) U.S. Cl. .......................... 422/58; 422/61; 422/102; 422/104; 204/400; 204/407; 600/584; 436/808

(58) Field of Classification Search ................. 422/58, 422/61, 102, 104; 600/583, 584; 436/808; 204/400, 407, 403.2, 403.11
See application file for complete search history.

(56) References Cited

U.S. PATENT DOCUMENTS

| | | | |
|---|---|---|---|
| 1,744,195 A * | 1/1930 | Alland .................... 221/312 R |
| 2,641,358 A | 6/1953 | Santo | |
| 3,393,831 A | 7/1968 | Stewart | |
| 3,589,557 A | 6/1971 | Johnson | |
| D249,333 S * | 9/1978 | Stern ........................... D9/193 |
| 4,114,780 A | 9/1978 | Sharon | |
| 4,173,226 A * | 11/1979 | Shell ........................... 604/295 |
| 4,187,077 A | 2/1980 | Covington et al. | |
| 4,190,420 A | 2/1980 | Covington et al. | |
| RE30,895 E | 4/1982 | Butera | |
| 4,328,184 A | 5/1982 | Kondo | |
| 4,717,018 A | 1/1988 | Sacherer | |
| 4,817,820 A | 4/1989 | Heiland | |
| 4,911,344 A | 3/1990 | Kahler | |
| 5,328,082 A | 7/1994 | Fritz et al. | |
| 5,409,133 A | 4/1995 | Gringer | |
| 5,489,414 A | 2/1996 | Schreiber et al. | |
| 5,510,266 A | 4/1996 | Bonner et al. | |

(Continued)

FOREIGN PATENT DOCUMENTS

DE    299 05 581 U1    3/1999

(Continued)

*Primary Examiner*—Monique T. Cole
(74) *Attorney, Agent, or Firm*—Kagan Binder, PLLC

(57) ABSTRACT

Devices for dispensing test strips and methods of using the same are provided. The subject devices are characterized by having a base and a cover, where the cover includes a test strip selecting element. The subject devices may also be characterized by having a test strip holding means, which may include a cover with resiliently deformable walls and/or a gravity controlled test strip holding mechanism. In the subject methods, a test strip container with at least one test strip is provided and placed into a position that causes at least one test strip contained in the base to move into the cover so that a single test strip is selected for use. The subject methods may also include positioning the device in a particular orientation that causes a selected test strip to be held in a fixed position. The subject invention also includes kits which include the subject devices.

75 Claims, 15 Drawing Sheets

U.S. PATENT DOCUMENTS

| | | |
|---|---|---|
| 5,534,224 A | 7/1996 | Abe |
| 5,575,403 A | 11/1996 | Charlton et al. |
| 5,630,986 A | 5/1997 | Charlton et al. |
| 5,678,729 A * | 10/1997 | Raymond .................... 222/23 |
| 5,757,666 A | 5/1998 | Schreiber et al. |
| 5,759,010 A | 6/1998 | Jacobs et al. |
| 5,797,693 A | 8/1998 | Jaeger |
| 5,863,800 A | 1/1999 | Eikmeier et al. |
| 5,871,452 A | 2/1999 | Baker et al. |
| 5,939,329 A * | 8/1999 | Christner et al. ........... 436/165 |
| 5,971,941 A | 10/1999 | Simons et al. |
| 6,036,924 A | 3/2000 | Simons et al. |
| 6,228,100 B1 | 5/2001 | Schraga |
| 6,485,918 B1 * | 11/2002 | Schermer et al. .............. 435/6 |

FOREIGN PATENT DOCUMENTS

| | | |
|---|---|---|
| EP | 0 308 770 | 9/1988 |
| WO | WO 94/10558 | 5/1994 |
| WO | WO 98/47007 | 10/1998 |
| WO | WO99/44508 | 9/1999 |
| WO | WO 01/23885 | 4/2001 |
| WO | WO 0163272 | 8/2001 |
| WO | WO 02/08753 | 1/2002 |

* cited by examiner

TEST STRIP CONTAINERS AND METHODS OF USING THE SAME

FIELD OF THE INVENTION

The field of this invention is test strip containers.

BACKGROUND OF THE INVENTION

Analyte concentration determination in physiological samples is of ever increasing importance to today's society. Such assays find use in a variety of application settings, including clinical laboratory testing, home testing, etc., where the results of such testing play a prominent role in the diagnosis and management of a variety of disease conditions. Analytes of interest include glucose for diabetes management, cholesterol for monitoring cardiovascular conditions, and the like. In response to this growing importance of analyte concentration determination, a variety of analyte concentration determination protocols and devices for both clinical and home testing have been developed.

Before testing can begin, an individual seeking to determine the presence and/or concentration of an analyte in a physiological sample must first obtain a test strip, apply a sample thereto and obtain the results either manually or automatically with a meter or the like. However, obtaining a test strip to begin the procedure is not without difficulty. The ability to easily obtain a test strip, particularly a single test strip from amongst a plurality of test strips is important particularly for those containers and test strips that will be used by persons with diminished hand-eye coordination or finger sensation. For example, persons with diabetes typically have either or both impaired vision and diminished finger sensation or other dexterity problems. Such persons must use test strips to test their blood glucose levels a number of times a day. However, the typical test strip is only several millimeters in width and length and, thus, difficult to manipulate.

The simplest test strip containers are simple storage reservoirs where the test strips are retained inside and manually removed. However, it is difficult to easily extract a test strip from these containers. These containers are usually shaped and sized to hold a plurality of test strips and to completely encompass the test strips inside so as to protect the test strips from light, humidity, and other environmental contaminants including oils and the like from an individual's hands, where such protection is necessary to insure the precision, accuracy and overall integrity of the test result.

An exemplary embodiment of such a simple test strip container is shown in FIG. 1. To obtain a single test strip from the container to begin a test, an individual has two options for removing a test strip. In one option, an individual may simply turn the container upside down to pour a test strip out. This, as is apparent, has significant disadvantages as one or all of the test strips stored inside the container may quickly spill out and become contaminated or damaged. In a second option, an individual places a finger inside the container to try to grasp a single test strip amongst a plurality of test strips without damaging or contaminating any of the strips in the process. However, such a method is difficult for individuals who have either or both impaired vision and diminished finger sensation and oftentimes results in an individual inadvertently contacting portions of the test strip that should not be touched, such as testing or reaction areas (i.e., areas on the strip having testing reagents, etc.) and the like, where such contact can impart contaminants and cause erroneous testing results. Similarly, other test strips may be inadvertently contacted resulting in erroneous testing results of those test strips as well. Furthermore, the container must have a suitable shape and a large enough size to accommodate at least one finger therein for easy removal of a test strip. In other words, the container must enable an individual, i.e., an individual who may be visually and/or dextrally impaired, to retrieve a test strip from amongst a plurality of test strips without damaging or contaminating any of such test strips.

It can be appreciated that the container, while maintaining a size large enough to serve its functions, must be small enough to enable portability of the container so that an individual may easily carry the container at all times to accommodate testing during the course of a day. Due to the above described shape and size requirements, conventional containers are typically cylindrical, i.e., have a circular cross-sectional shape, to accommodate insertion of at least one finger therein, and have a height of about 60 mm and a diameter of about 25 mm and are commercially sold with about 25 test strips retained therein. Such size and shape creates a great amount of unused space inside the container, minimizes the portability of the container and adds to the container's costs. In other words, the containers are larger than necessary to simply hold the test strips, thus increasing costs and decreasing portability.

More complex test strip containers have been developed to try to overcome some of the disadvantages associated with the simple test strip containers described above (see for example U.S. Pat. Nos. 5,575,403, 5,489,414; 5,630,986; 5,510,266). However, these, too, have certain disadvantages. For example, these devices often require a degree of physical dexterity and visual acuity that may be lacking in certain individuals who use the containers. Also, due to the complexity of the devices, i.e., the numbers of components forming the containers, the cost of manufacture increases and thus the cost to the user increases.

As such, there is continued interest in the development of new devices and methods for use in test strip dispensing. Of particular interest would be the development of such devices and methods which are easy and inexpensive to manufacture, have minimal components, are easy to use, particularly for visually and dextrally impaired individuals, are portable and which minimize damage and/or contamination to the test strips contained therein.

SUMMARY OF THE INVENTION

Devices for dispensing test strips and methods of using the same are provided. The subject devices are characterized by having a base and a cover, where the cover includes a test strip selecting element. The subject devices may also be characterized by having a test strip holding means, which may include one or both of a cover with resiliently deformable walls and a gravity controlled test strip holding mechanism. In the subject methods, a test strip container with at least one test strip is provided and placed into a position that causes at least one test strip contained in the base to move into the cover so that a single test strip is selected for use. The subject methods may also include positioning the device in a particular orientation that causes a selected test strip to be held in a fixed position. The subject invention also includes kits which include the subject devices.

BRIEF DESCRIPTION OF THE DRAWINGS

FIG. 10A illustrates an exemplary embodiment of a subject device in an appropriate position which causes a plurality of test strips contained in the base to move into the test strip selecting element of the cover, i.e., a substantially upside down position;

FIG. 10B illustrates an exemplary embodiment of a subject device having a gravity controlled test strip holding mechanism and appropriately positioned to cause a plurality of test strips contained in the base to move into the test strip selecting element of the cover, i.e., a substantially upside down position;

FIG. 10C illustrates the device of FIG. 10A having the cover separated from the base such that a selected test strip may be accessed;

FIG. 10D illustrates the device of FIG. 10A having walls thereof resiliently deformed to hold a selected test strip therebetween;

FIG. 10E illustrates the device of FIG. 10C having the cover separated from the base such that a selected and held test strip may be accessed;

FIG. 10F illustrates the device of FIG. 10B in a substantially upright position with a selected test strip held in a fixed position by the gravity controlled test strip holding mechanism; and FIG. 10G illustrates the device of FIG. 10F having the cover separated from the base such that a selected test strip may be accessed.

DETAILED DESCRIPTION OF THE INVENTION

Figure 1:
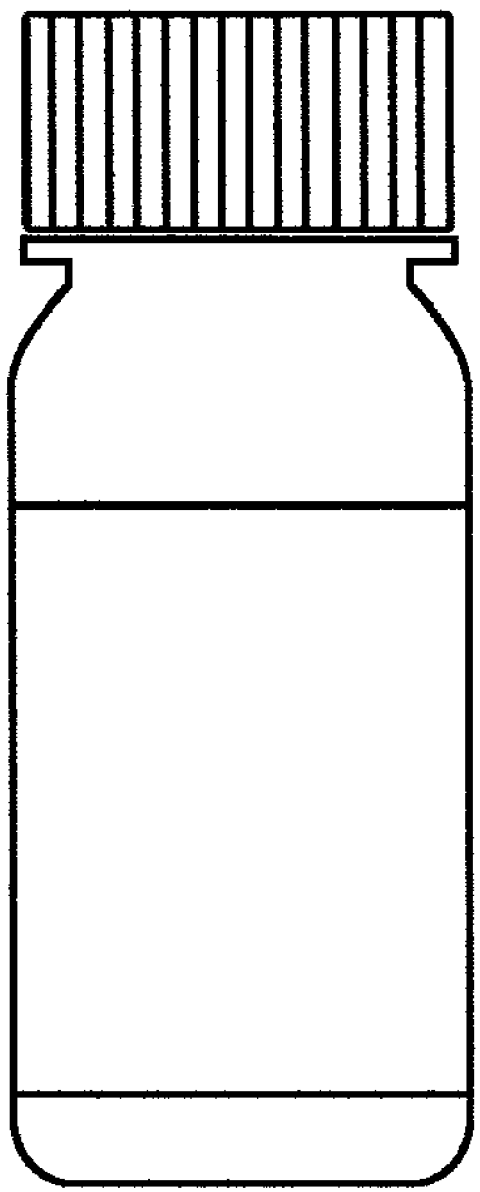
FIG. 1 shows an exemplary embodiment of a conventional test strip container.

Devices for dispensing test strips and methods of using the same are provided. The subject devices are characterized by having a base and a cover, where the cover includes a test strip selecting element. The subject devices may also be characterized by having a test strip holding means, which may include one or both of a cover with resiliently deformable walls and a gravity controlled test strip holding mechanism. In the subject methods, a test strip container with at least one test strip is provided and placed into a position that causes at least one test strip contained in the base to move into the cover so that a single test strip is selected for use. The subject methods may also include positioning the device in a particular orientation that causes a selected test strip to be held in a fixed position. The subject invention also includes kits which include the subject devices.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a reagent" includes a plurality of such reagents and reference to "the device" includes reference to one or more devices and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the subject invention, the subject devices are described first. Next, a description of the subject methods is provided, followed by a review of kits which include the subject devices.

Devices

As summarized above, devices are provided for containing and dispensing test strips. Particularly, devices are provided for containing one or more test strips and easily dispensing a test strip therefrom for use and usually the subject devices provide for the easy dispensation of a single test strip from amongst a plurality of test strips, i.e., dispenses each test strip separately or one test strip at a time.

The subject invention is suitable for dispensing any type of test strip, for example electrochemical and colorimetric or photometric (i.e., optical) type test strips as are known in the art, where such test strips find use in the determination of a wide variety of different analyte concentrations and where representative analytes include, but are not limited to, glucose, cholesterol, lactate, alcohol, and the like. In many embodiments, the test strips used with the subject invention are used to determine the glucose concentration in a physiological sample, e.g., interstitial fluid, blood, blood fractions, constituents thereof, and the like. In further describing the subject invention, a review of representative colorimetric (also commonly referred to as photometric and optical) and electrochemical test strips is provided first to provide a proper foundation for the subject invention, where such a review is by way of example and is not intended to limit the scope of the invention. In other words, it will be apparent that a wide variety of test strips, including, but not limited to, the representative colorimetric and electrochemical test strips described herein, may be suitable for use with the present invention. The review of suitable test strips is followed by a description of the subject test strip container devices and the subject methods. Finally, a description of kits that include the subject test strip container devices is provided.

Representative Colorimetric Test Strips

Figure 2A:
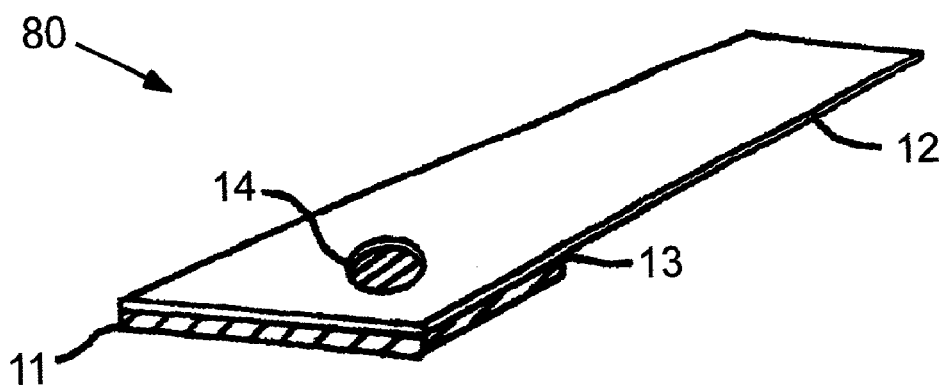
FIG. 2A shows an exemplary embodiment of a representative colorimetric test strip suitable for use with the subject invention.

The colorimetric or photometric or optical (herein used interchangeably) reagent test strips employed in these embodiments of the subject invention are generally made up of at least the following components: a matrix 11 for receiving a sample, a reagent composition (not shown as a structural component) that typically includes one or more members of an analyte oxidation signal producing system and a support element 12. The colorimetric test strips are usually configured and adapted to be received in an automated meter, as described below, for automatically determining the concentration of an analyte. An exemplary embodiment of a representative colorimetric test strip is shown in FIG. 2A. FIG. 2A shows colorimetric test strip 80 in which a matrix 11 is positioned at one end of support element 12 with an adhesive 13. A hole 14 is present in the support element 12 in the area of matrix 11 in which a sample can be applied to one side of the matrix 11 and a reaction can be detected on an opposite side of matrix 11. The components of an exemplary colorimetric test strip will now be described in more detail.

Matrix

Matrix 11 that is employed in the subject test strips is an inert matrix which provides a support for the various members of the signal producing system, described below, as well as the light absorbing or chromogenic product produced by the signal producing system, i.e., the indicator. Matrix 11 is configured to provide a location for the physiological sample, e.g., blood, application and a location for the detection of the light-absorbing product produced by the indicator of the signal producing system. As such, matrix 11 is one that is permissive of aqueous fluid flow through it and provides sufficient void space for the chemical reactions of the signal producing system to take place. A number of different matrices have been developed for use in various analyte detection assays, which matrices may differ in terms of materials, dimensions and the like, where representative matrices include, but are not limited to, those described in U.S. Pat. Nos.: 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; 5,968,836 and 5,972,294; the disclosures of which are herein incorporated by reference. In principle, the nature of matrix 11 is not critical to the subject test strips and therefore is chosen with respect to other factors, including the nature of the instrument which is used to read the test strip, convenience and the like. As such, the dimensions and porosity of the test strip may vary greatly, where matrix 11 may or may not have pores and/or a porosity gradient, e.g. with larger pores near or at the sample application region and smaller pores at the detection region. Materials from which matrix 11 may be fabricated vary, and include polymers, e.g. polysulfone, polyamides, cellulose or absorbent paper, and the like, where the material may or may not be functionalized to provide for covalent or non-covalent attachment of the various members of the signal producing system.

Signal Producing System

In addition to matrix 11, the subject test strips further include one or more members of a signal producing system which produces a detectable product in response to the presence of analyte, which detectable product can be used to derive the amount of analyte present in the assayed sample. In the subject test strips, the one or more members of the signal producing system are associated, e.g., covalently or non-covalently attached to, at least a portion of (i.e., the detection region) the matrix, and in many embodiments to substantially all of the matrix.

In certain embodiments, e.g., where glucose is the analyte of interest, the signal producing system is an analyte oxidation signal producing system. By analyte oxidation signal producing system is meant that in generating the detectable signal from which the analyte concentration in the sample is derived, the analyte is oxidized by one or more suitable enzymes to produce an oxidized form of the analyte and a corresponding or proportional amount of hydrogen peroxide. The hydrogen peroxide is then employed, in turn, to generate the detectable product from one or more indicator compounds, where the amount of detectable product generated by the signal measuring system, i.e. the signal, is then related to the amount of analyte in the initial sample. As such, the analyte oxidation signal producing systems present in the subject test strips are also correctly characterized as hydrogen peroxide based signal producing systems.

As indicated above, the hydrogen peroxide based signal producing systems include an enzyme that oxidizes the analyte and produces a corresponding amount of hydrogen peroxide, whereby corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the first enzyme may be: glucose oxidase (where the analyte is glucose); cholesterol oxidase (where the analyte is cholesterol); alcohol oxidase (where the analyte is alcohol); lactate oxidase (where the analyte is lactate) and the like. Other oxidizing enzymes for use with these and other analytes of interest are known to those of skill in the art and may also be employed. In those preferred embodiments where the reagent test strip is designed for the detection of glucose concentration, the first enzyme is glucose oxidase. The glucose oxidase may be obtained from any convenient source, e.g. a naturally occurring source such as *Aspergillus niger* or *Penicillum*, or recombinantly produced.

A second enzyme of the signal producing system may be an enzyme that catalyzes the conversion of one or more indicator compounds into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Y. Ci, F. Wang; Analytica Chimica Acta, 233 (1990), 299–302.

The indicator compound or compounds, e.g., substrates, are ones that are either formed or decomposed by the hydrogen peroxide in the presence of the peroxidase to produce an indicator dye that absorbs light in a predetermined wavelength range. Preferably the indicator dye absorbs strongly at a wavelength different from that at which the sample or the testing reagent absorbs strongly. The oxidized form of the indicator may be a colored, faintly-colored, or colorless final product that evidences a change in color of the testing side of the membrane. That is to say, the testing reagent can indicate the presence of glucose in a sample by a colored area being bleached or, alternatively, by a colorless area developing color.

Indicator compounds that are useful in the present invention include both one- and two-component chromogenic substrates. One-component systems include aromatic amines, aromatic alcohols, azines, and benzidines, such as tetramethyl benzidine-HCl. Suitable two-component systems include those in which one component is MBTH, an MBTH derivative (see for example those disclosed in U.S. patent application Ser. No. 08/302,575, incorporated herein by reference), or 4-aminoantipyrine and the other component is an aromatic amine, aromatic alcohol, conjugated amine, conjugated alcohol or aromatic or aliphatic aldehyde. Exemplary two-component systems are 3methyl-2-benzothiazolinone hydrazone hydrochloride (MBTH) combined with 3-dimethylaminobenzoic acid (DMAB); MBTH combined with 3,5-dichloro-2-hydroxybenzene-sulfonic acid (DCHBS); and 3-methyl-2-benzothiazolinonehydrazone N-sulfonyl benzenesulfonate monosodium (MBTHSB) combined with 8-anilino-1 naphthalene sulfonic acid ammonium (ANS). In certain embodiments, the dye couple MBTHSB-ANS is preferred.

In yet other embodiments, signal producing systems that produce a fluorescent detectable product (or detectable non-fluorescent substance, e.g. in a fluorescent background) may be employed, such as those described in: Kiyoshi Zaitsu, Yosuke Ohkura: New fluorogenic substrates for Horseradish Peroxidase: rapid and sensitive assay for hydrogen peroxide and the Peroxidase. Analytical Biochemistry (1980) 109, 109–113.

Support Element

Matrix 11 is usually attached to a support element 12. Support element 12 may be of a material that is sufficiently rigid to be inserted into an automated device such as a meter without undue bending or kinking. Matrix 11 may be attached to support element 12 by any convenient mechanisms, e.g., clamps, adhesive, etc., herein shown attached using an adhesive 13. In many embodiments, support member 12 is made of material such as polyolefins, e.g., polyethylene or polypropylene, polystyrene or polyesters. Consequently, the length of the support element 12 typically dictates or corresponds to the length of the test strip.

Regardless of whether or not the length of support element 12 dictates or corresponds to the length of test strip 80, the total length of the test strip 80 generally ranges from about 5 mm to about 80 mm, usually from about 15 mm to about 65 mm and more usually from about 40 mm to about 55 mm, the width of the test strip 80 typically ranges from about 2 mm to about 35 mm, usually from about 5 mm to about 20 mm and more usually from about 7 mm to about 15 mm and the thickness of the test strip 80 typically ranges from about 0.2 mm to about 7.5 mm, usually from about 0.4 mm to about 2.0 mm and more usually from about 0.6 mm to about 1.5 mm.

As described above, support element 12 is usually configured to enable test strip 80 to be used with or inserted into a meter. As such, support element 12, and thus test strip, is typically in the form of a substantially rectangular or square-like strip, where the dimensions of support element 12 vary according to a variety of factors, as will be apparent to those of skill in the art.

In using such a colorimetric test strip, sample is allowed to react with the members of the signal producing system to produce a detectable product that is present in an amount proportional to the initial amount present in the sample. The amount of sample that is introduced to matrix 11 of the test strip may vary, but generally ranges from about 0.1 to 25 µl, usually from about 5 to 10 µl. The sample may be introduced to matrix 11 using any convenient protocol, where the sample may be injected, allowed to wick, or be otherwise introduced. The amount of detectable product, i.e., signal produced by the signal producing system, is then determined and related to the amount of analyte in the initial sample. In certain embodiments, automated meters that perform the above mentioned detection and relation steps are employed. The above described reaction, detection and relating steps, as well as instruments for performing the same, are further described in U.S. Pat. Nos. 4,734,360; 4,900,666; 4,935, 346; 5,059,394; 5,304,468; 5,306,623; 5,418,142; 5,426, 032; 5,515,170; 5,526,120; 5,563,042; 5,620,863; 5,753, 429; 5,573,452; 5,780,304; 5,789,255; 5,843,691; 5,846, 486; 5,968,836 and 5,972,294; the disclosures of which are herein incorporated by reference.

Examples of such colorimetric reagent test strips that may be used with the subject invention include, but are not limited to, those described in U.S. Pat. Nos. 5,049,487; 5,563,042; 5,753,452; 5,789,255, the disclosures of which are herein incorporated by reference.

Representative Electrochemical Test Strips

Figure 2B:
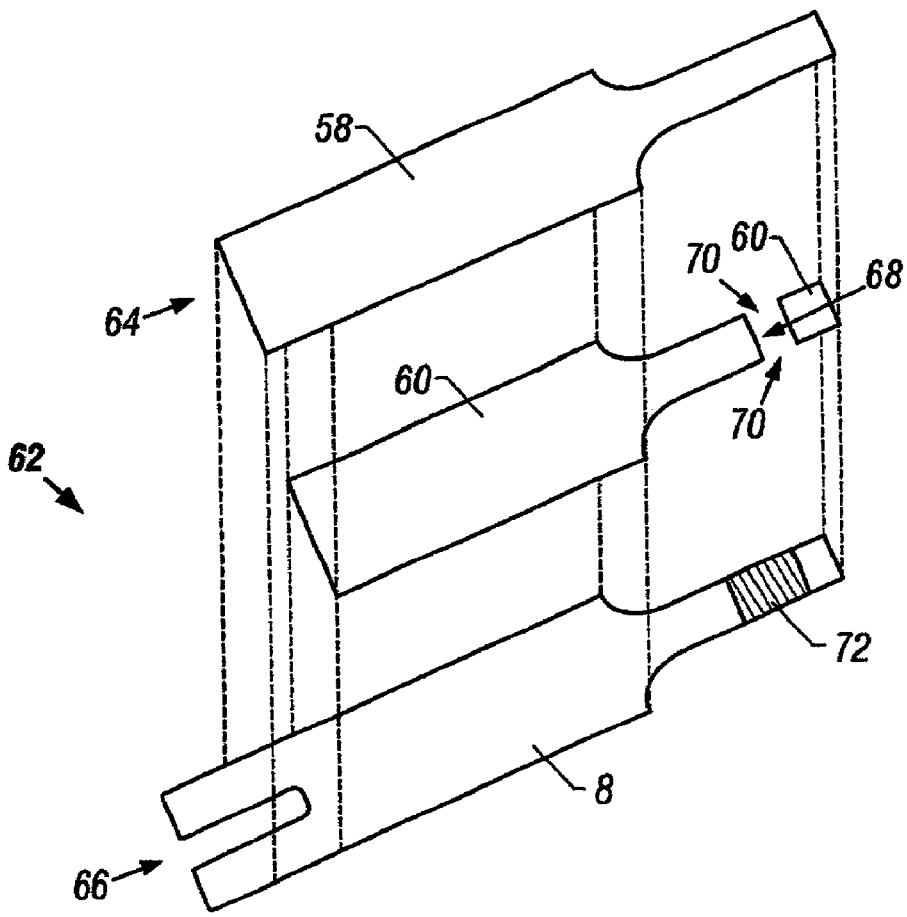
FIG. 2B shows an exploded view of an exemplary embodiment of a representative electrochemical test strip suitable for use with the subject invention.

Generally, the electrochemical test strips that find use with the subject invention are made up of two opposing metal electrodes separated by a thin spacer layer. In many embodiments a redox reagent system is located in the reaction area or zone. The electrochemical test strips may be configured and adapted to be received in an automated meter, as described below, for automatically determining the concentration of an analyte. FIG. 2B shows an exploded view of an exemplary embodiment of a representative electrochemical test strip. Test strip 62 includes a reference electrode 64 and a working electrode 66 separated by a spacer layer 60 which is cut away to define a reaction area or zone 68 in communication with side ports 70 defined by a break in the spacer layer's coverage adjacent reagent system or composition 72.

The working electrode 66 and reference electrode 64 are further characterized in that at least the surfaces of the electrodes that face the reaction area 68 of the electrochemical cell in the strip is a metal, where metals of interest include palladium, gold, platinum, silver, iridium, carbon (conductive carbon ink), doped tin oxide, stainless steel and the like. In many embodiments, the metal is gold or palladium.

While in principle the entire electrode may be made of a metal, each of the electrodes is generally made up of an inert support material on the surface of which is present a thin layer of the metal component of the electrode. Any convenient inert support material may be employed in the subject electrodes, where typically the material is a rigid material that is capable of providing structural support to the electrode and, in turn, the electrochemical test strip as a whole. Suitable materials that may be employed as the inert support material include plastics, e.g., polyethylene terephthalate (PET), polyethylene terephthalate glycol modified (PETG), polyimide, polycarbonate, polystyrene, silicon, ceramic, glass, and the like. In some instances, the support itself may be made of metal, especially one of those noted above. Generally, however, the electrode is a composite of a support coated with a metallic and/or conductive coating (such as palladium, gold, platinum, silver, iridium, carbon conductive carbon ink doped tin oxide or stainless steel).

When a metal-coated support is to be employed, its thickness (metal and support) will typically range from about 0.002 to about 0.014 in (about 51 µm to about 356 µm), usually from about 0.004 to about 0.007 in (about 102 µm to about 178 µm), while the thickness of the metal layer will typically range from about 10 to 300 nm and usually from about 20 to 40 nm.

As depicted, the working and reference electrodes 66 and 64, respectively, are generally configured in the form of elongate strips. Typically, the length of the electrodes ranges from about 0.64 cm to about 7.6 cm, usually about 2.0 cm to about 3.8 cm. The width of the electrodes typically ranges from about 0.025 cm to about 0.76 cm, usually from about 0.25 cm to about 0.67 cm. In certain embodiments, the length of one of the electrodes is shorter than the other. Oftentimes, the electrode and spacer width is matched where the elements overlap. In certain embodiments, electrode 64 is about 3.5 cm long, electrode 66 is about 3.8 cm long, and each are about 6.4 mm wide at their maximum and about 2.6 mm wide at their minimum, reaction zone 68 and ports 70 are about 1.65 mm wide and the reaction zone 68 has an area of about 0.041 cm$^2$. Spacer 60 incorporated in the strip may be set back, e.g., about 7.6 mm from the end of electrode 66.

The reaction area or zone 68 in which activity occurs preferably has a volume of at least about 0.1 µl, usually at least about 0.3 µl and more usually at least about 0.6 µl, where the volume may be as large as 10 µl or larger. The size of zone 68 is largely determined by the characteristics of spacer layer 60. While spacer layer 60 is shown to define a rectangular reaction area in which the aforementioned activity occurs, other configurations are possible, (e.g., square, triangular, circular, irregular-shaped reaction areas, etc.). The thickness of spacer layer 60 generally ranges from about 25 µm to about 500 µm, usually from about 76 µm to about 127 µm, thus the total thickness of the test strip (electrodes and spacer layer) typically ranges from about 127 µm to about 1270 µm, usually from about 254 µm to about 762 µm and more usually from about 380 µm to about 510 µm. The manner in which spacer layer 60 is cut also determines the characteristics of ports 70. The cross-sectional area of inlet and outlet ports 70 may vary as long as it is sufficiently large to provide an effective entrance or exit of fluid from reaction area 68.

As mentioned above, in many embodiments a reagent system or composition 72 is present in the reaction area, where reagent system 72 interacts with components in the fluid sample during the assay. Reagent systems of interest typically include a redox couple. The redox couple of the reagent composition, when present, is made up of one or more redox couple agents. A variety of different redox couple agents are known in the art and include: ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, ruthenium complexes, and the like. Other reagents that may be present in the reaction area include buffering agents, e.g., citraconate, citrate, malic, maleic, phosphate, "Good" buffers and the like. Yet other agents that may be present include: divalent cations such as calcium chloride, and magnesium chloride; surfactants such as Triton, Macol, Tetronic, Silwet, Zonyl, and Pluronic; stabilizing agents such as albumin, sucrose, trehalose, mannitol, and lactose. Examples of such a reagent test strips suitable for use with the subject invention include those described in U.S. Pat. No. 6,193,873 and copending and commonly owned U.S. application Ser. Nos. 09/497,304; 09/497,269; 09/736,788 and 09/746,116, the disclosures of which are herein incorporated by reference.

To use such an electrochemical test strip, an aqueous liquid sample (e.g., blood) is placed into the reaction zone. The amount of physiological sample that is introduced into the reaction area of the test strip may vary, but generally ranges from about 0.1 to 10 µl, usually from about 0.3 to 0.6 µl. The sample may be introduced into the reaction area using any convenient protocol, where the sample may be injected into the reaction area, allowed to wick into the reaction area, or be otherwise introduced through the ports. The component to be analyzed is allowed to react with the redox reagent coating to form an oxidizable (or reducible) substance in an amount corresponding to the concentration of the component to be analysed (i.e., analyte). The quantity of the oxidizable (or reducible) substance present is then estimated by an electrochemical measurement. The measurement that is made may vary depending on the particular nature of the assay and the device with which the electrochemical test strip is employed (e.g. depending on whether the assay is coulometric, amperometric or potentiometric). Measurement with strip 62 is preferably accomplished by way of an automated instrument or meter. Usually, measurement is taken over a given period of time following sample introduction into the reaction area. Methods for making electrochemical measurements are further described in U.S. Pat. Nos.: 4,224,125; 4,545,382; and 5,266,179; as well as WO 97:/18465 and WO 99/49307 publications, the disclosures of which are herein incorporated by reference.

Following detection of the electrochemical signal generated in the reaction zone, as described above, the amount of the analyte present in the sample introduced into the reaction zone is then typically determined by relating the electrochemical signal to the amount of analyte in the sample. In making this derivation, the measures electrochemical signal is usually compared to the signal generated from a series of previously obtained control or standard values, and determined from this comparison. In many embodiments, the electrochemical signal measurement steps and analyte concentration derivation steps, are performed automatically by a device designed to work with the test strip to produce a value of analyte concentration in a sample applied to the test strip, as noted above. A representative reading device for automatically practicing these steps, such that user need only apply sample to the reaction zone and then read the final analyte concentration result from the device, is further described in copending U.S. application Ser. No. 09/333,793 filed Jun. 15, 1999, the disclosure of which is herein incorporated by reference.

Test Strip Containers

As described above, the subject invention includes devices that contain and easily dispense a test strip, such as the type of test strip described above, where the subject test strip container devices have minimal components and prevent or minimize test strip contact with adverse contaminants such as dirt and oils or other contaminants from human hands, etc. Typically, the subject devices dispense a single test strip from a plurality or aggregate of contained test strips. Usually the subject devices are configured to retain from about 1 to about 50 test strips at one time, usually about 5 to about 40 test strips at one time and more usually from about 10 to about 25 test strips at one time, however the subject devices may be configured to retain a greater or fewer number of test strips at one time. The subject devices also allow for easy re-loading of additional test strips, as will be apparent from the descriptions below. In further describing the invention, electrochemical test strips of the type described above will be used herein for exemplary purposes and is in no way intended to limit the scope of the invention.

Figure 3A:
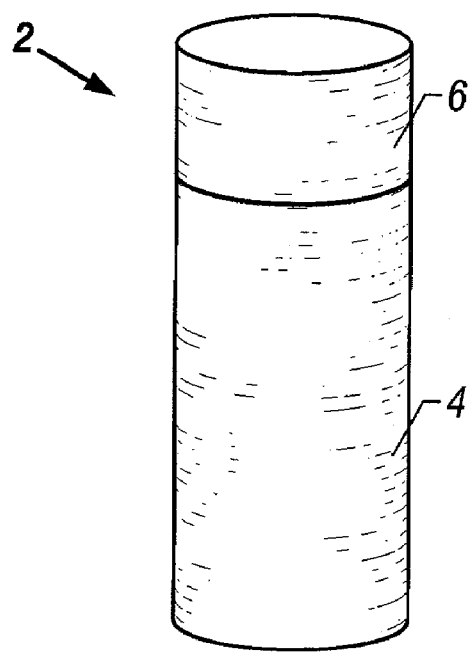
FIG. 3A shows an exemplary embodiment of a subject test strip container according to the subject invention.

The subject test strip dispenser devices will now be described with reference to the Figures, where like numerals represent like components or features. FIG. 3A shows the exterior of an exemplary embodiment of a subject test strip container 2 having a base 4 and a cover 6 and having a cylindrical shape. Cover 6 and base 4 are removably connected or associated to each other using any convenient means, for example they may be associated using corresponding threads, a hinge, friction, a snap fit, etc., or any combination thereof and may include a gasket therebetween in certain embodiments. Base 4 and cover 6 will be associated such that cover 6 may be readily and easily separated from base 4.

Figure 3B:
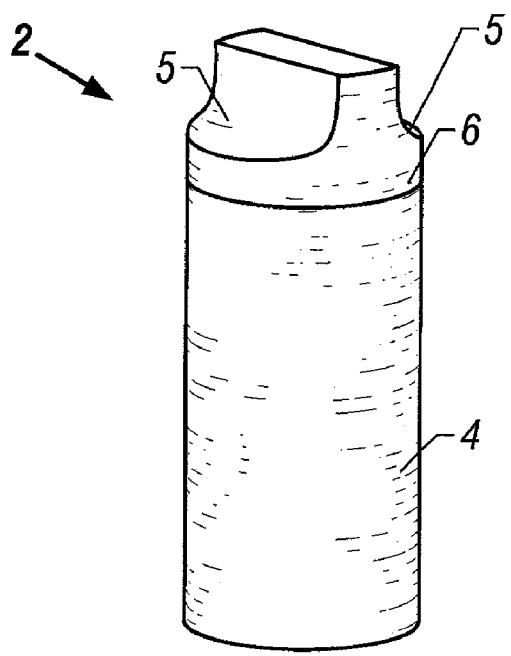
FIG. 3B shows the test strip container of FIG. 3A having indents on the cover.

The shape of container 2 will necessarily vary depending on a variety of factors, where such factors include, but are not limited to, the type, size and number of test strips retained therein, and the like. FIG. 3A shows test strip container 2 having a cylindrical shape, but other shapes are possible as well. Accordingly, the shape of container 2 may have any of a variety of shapes ranging from simple to complex, where the shape of base 4 may differ from the shape of cover 6. For example, base 4 of the container 2 may be of a rectangular, square, cylindrical, circular, elliptical or oval shape, etc., or substantially so. Alternatively, as mentioned, the shape of base 4 may be more complex such as a substantially irregular shape or the like. The shape of cover 6 may also assume a variety of shapes such as those described above with reference to base 4. In certain embodiments, cover 6 will assume a substantially irregular shape as shown in FIG. 3B. FIG. 3B shows cover 6 of FIG. 3A having a somewhat irregular shape due to tapered portions or indents 5 positioned on opposing sides of cover 6, where indents 5 enable an individual to easily grasp and hold cover 6 and in certain embodiments at least those walls that include indents 5 are resiliently deformable walls as will be described in greater detail below.

Likewise, the size of test strip container 2 may also vary depending on a variety of factors such as the type, size and number of test strips retained therein, and the like. Container 2 is configured such that the plurality of test strips is held primarily in base portion 4 of container 2 when container 2 is substantially upright. Container 2 will typically be sized to be easily held and transported by an individual. By way of example only and not limitation, in certain embodiments, the length of container 2 typically ranges from about 12 mm to about 100 mm, usually from about 25 mm to about 75 mm and more usually from about 35 to about 51 mm and the width/diameter of the container 2 ranges from about 10 mm to about 40 mm, usually from about 15 mm to about 35 mm and more usually from about 20 to about 25 mm.

The container 2 may be manufactured from a variety of materials, where the base 4 and cover 6 of the container 2 may be manufactured from the same or different materials, but where such materials will not substantially interfere with the testing reagents of the test strips retained therein. In certain embodiments, a portion of the container 2 may be made of a resiliently deformable or flexible material. For example, in certain embodiments, at least cover 6 or at least one or more walls thereof may be made of a material that is easily resiliently deformable or flexible such that the one or more walls may be deformed upon slight pressure applied by an individual thereto and where the walls will assume their original configuration upon release of the pressure thereto, as will be described in greater detail below. Representative materials that may be used in subject container 2 include, but are not limited to, polymeric materials such as polytetrafluoroethylene, polypropylene, polyethylene, polystyrene, polycarbonate and blends thereof, metals such as stainless steel, aluminum and alloys thereof, Teflon™, siliceous material, e.g., glass materials, and the like.

In certain embodiments of the subject containers, base 4 and cover 6 are associated or alignable in a closed configuration such that the device is substantially or completely air and moisture tight when in such a closed configuration. In other words, the interior of container 2 is substantially air and moisture tight when base 4 and cover 6 are brought together to form a closed container 2.

The subject container 2 may further include moisture absorbent reagents or components such as desiccant material, silica gel and the like, where such material is capable of absorbing moisture from the environment surrounding the stored test strips. Such absorbent reagents or components may be retained in one or more compartments positioned inside cover 6 and/or base 4.

As mentioned above, the subject test strip containers are capable of dispensing a single test strip at one time for use. Accordingly, a feature of the subject devices is the presence of a test strip selecting element 20 (see FIG. 4) that is capable of selecting a single test strip 30a contained in the subject container 2 so that it may be used. That is, where a subject container 2 contains a plurality of test strips, test strip selecting element 20 is capable of easily selecting a single test strip 30a, i.e., it separates a single test strip 30a from other test strips 30, and positions it for use. Test strip selecting element 20 operates by simple manipulation or handling of a subject container 2, i.e., it does not require an individual to actuate the device or any component thereof, and thus is passively activated and particularly well suited for an individual who has dexterity problems such as diminished fingertip sensation and/or is visually impaired.

Accordingly, test strip selecting element 20 selects and positions a test strip 30a for use when container 2 is positioned in a particular orientation relative to the ground. More specifically, the test strip selecting element 20 selects and positions a test strip 30a by a simple rotation or turning of container 2 to a substantially upside down position. In many embodiments, the subject container 2 also includes a test strip holding means for holding a test strip, such as a test strip that has been selected by a test strip selecting element, in a fixed position relative to cover 6. The test strip holding means also does not require an individual to actuate the device or any component thereof, i.e., is passively activated. Test strip selecting element 20 will now be described in greater detail, followed by a description of the subject test strip holding means.

Test Strip Selecting Element

As described above, test strip container 2 includes test strip selecting element 20 positioned in cover 6. In many embodiments, test strip selecting element 20 selects a test strip 30*a* to be held by a test strip holding means, as will be described in more detail below. In those embodiments where container 2 contains a plurality of test strips 30, test strip selecting element 20 selects or separates a single test strip 30*a* from the plurality or aggregate of test strips 30. More specifically, test strip selecting element 20 includes an area or cavity 25 that has a continuously reduced diameter or continuously reduced cross-sectional area. As such the shape of cavity 25 may be characterized as substantially frustum-shaped. Substantially frustum-shaped cavity 25 includes first end 21 and second end 23. Substantially frustum-shaped cavity 25 opens on second end 23 that is in direct communication with base 4 and through which at least one test strip, and more usually a plurality of test strips, previously contained in the base 4 of the container 2 moves, so that a single test strip may be selected at first end 21 of test strip selecting element 20. In other words, test strip selecting element 20 funnels at least one test strip through a substantially frustum-shaped cavity 25 thereof so as to ultimately select a single test strip 30*a* in an opening or slot 22 of test strip selecting element 20. The remaining test strips 30 are prevented from passing all the way through test strip selecting element 20 to slot 22 and, as such, remain in cavity 25 of test strip selecting element 20 and/or base 4 until selected for later use by an individual.

The cross-sectional shape of continuously reduced diameter cavity 25 may vary depending on a variety of factors such as the size and shape of the test strip to be dispensed, etc., with the only limitation that cavity 25 is capable of funneling at least one test strip therethrough. For example, the cross sectional shape of substantially frustum-shaped cavity 25 may be rectangular, square, circular, elliptical, etc. Accordingly, the cross-sectional shapes of the exemplary embodiments of substantially frustum-shaped cavity 25 shown herein are for exemplary purposes only and are not intended to limit the scope of the invention.

Figure 4:
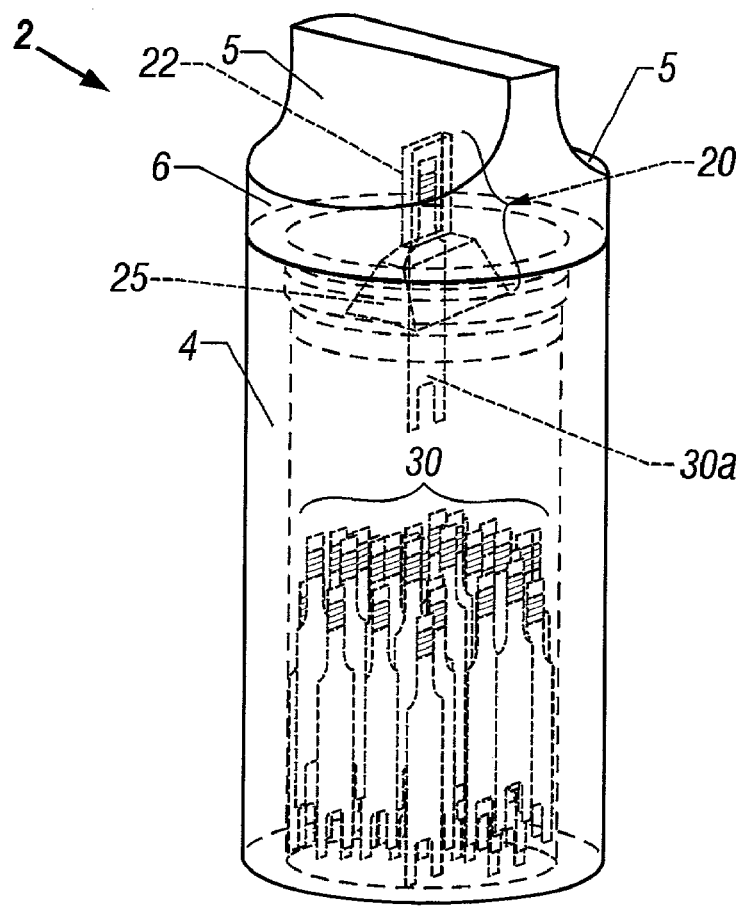
FIG. 4 shows a perspective view of a subject test strip container having a subject test strip selecting element.
Figure 5:
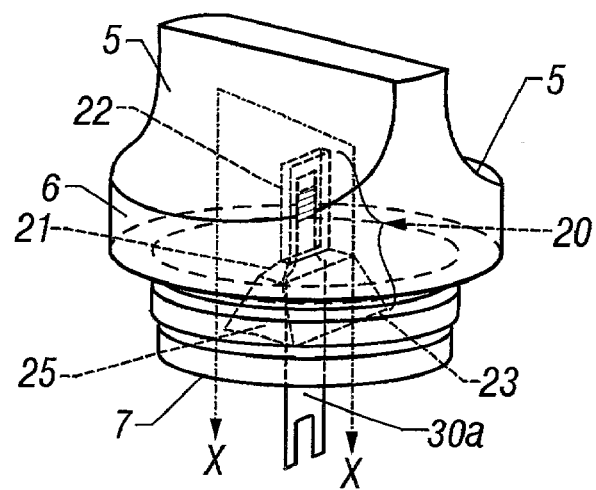
FIG. 5 shows an enlarged view of the cover of FIG. 4 having a test strip selected by the test strip selecting element.

Referring now to FIG. 5, which shows an enlarged view of cover 6 of FIG. 4 in a substantially upright position, test strip selecting element 20 is configured within cover 6 such that when container 2 is appropriately positioned, test strips 30 retained in base 4 move into test strip selecting element 20. By appropriate position is meant that the device is positioned substantially upside down. That is, if the device is originally oriented in a substantially upright orientation, then the device is turned or rotated so that the device is substantially upside down. By substantially upright is meant container 2 is at an angle β (see FIG. 9A) that ranges from about −30 to about +30 relative to the longitudinal axis $L_2$ of the container 2 when the longitudinal axis $L_2$ of the container 2 is positioned perpendicular to the ground G and base 4 is closer to ground G than cover 6 is positioned with respect to the ground G. By substantially upside down is meant container 2 is at an angle γ (see FIG. 9B) that ranges from about −20 to about +20 relative to the longitudinal axis $L_2$ of the container 2 when the longitudinal axis $L_2$ of the container 2 is positioned perpendicular to the ground G and the cover 6 is closer to the ground G than the base 4 is positioned with respect to the ground G.

As shown in FIG. 5, test strip selecting element 20 can be characterized as having a first end 21 that includes slot 22, a second end 23 positioned at opening 7 of cover 6 which is in direct communication with base 4, and a substantially frustum-shaped cavity 25 positioned between first end 21 and second end 23. Test strip selecting element 20 may be a unitary piece of construction with respect to cover 6, i.e., may be molded in cover 6, or may a separate component that is attached to the interior of cover 6 by any convenient means, including welding, adhesives, friction, snap fit, etc., and any combination thereof. Typically, test strip selecting element 20 will be a unitary piece of construction with respect to cover 6.

As mentioned above, cavity 25 of test strip selecting element 20 is substantially frustum shaped or funnel-like, i.e., has a substantially funnel shape such that it has walls that taper towards slot 22 of first end 21, e.g., a cone-like shape, although it need not be cylindrical in shape as long as the walls taper inwardly towards slot 22. As shown in FIG. 5, the diameter or cross sectional area of test strip selecting element 20 gradually decreases from second side 23 to slot 22 of first side 21. That is, the diameter of test strip selecting element 20 decreases to an ultimate diameter or area that only accommodates or is only permissive of a single test strip.

Figure 6:
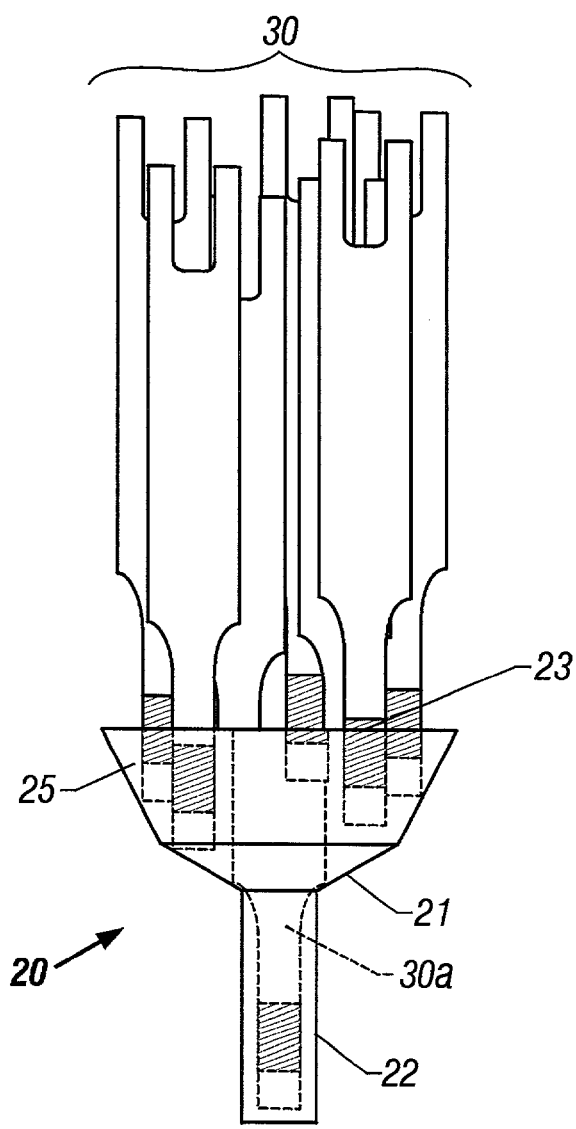
FIG. 6 shows an enlarged view of the test strip selecting element of FIG. 5 substantially upside down and having a single test strip selected therein.

FIG. 6 shows an enlarged view of test strip selecting element 20 of FIG. 5 in a substantially upside down position having a single test strip 30*a* selected in slot 22 from amongst a plurality of test strips 30. As shown, the substantially frustum or funnel-like shape of cavity 25 enables test strip selecting element 20 to select a single test strip 30*a* in slot 22 as the number of the test strips that are able to be accommodated in cavity 25 decreases from the second side 23 to the first side 21 when the device is appropriately positioned, such that ultimately one single test strip 30*a* is separated from the aggregate 30 and selected in slot 22, as shown in FIGS. 4, 5 and 6. The selected test strip 30*a* is positioned in slot 22 such that a portion of the test strip 30*a* resides in slot 22 and a portion protrudes or extends within or through cavity 25.

Slot 22 is sized and shaped for selecting or being permissive of only a single test strip therein at one time. However, the size and/or shape of slot 22 need not necessarily correspond to that of a test strip, i.e., the size and/or shape of slot 22 may differ from the size and/or shape (width) of a test strip, as long as slot 22 enables a single test strip to be selected thereby, e.g., a test strip may be rectangular in shape and slot 22 may be of a shape other than rectangular. By way of example only and not limitation, in certain embodiments when container 2 is used with test strips having lengths ranging from about 7 mm to about 76 mm, widths ranging from about 1.3 mm to about 7.6 mm and thicknesses ranging from about 127 µm to about 1270 µm, the length of slot 22 will typically range from about 3 mm to about 50 mm, usually from about 5 mm to about 25 mm and more usually from about 6 mm to about 10 mm, the width of slot 22 (in this embodiment configured to accommodate the narrow portion of the test strip) will typically range from about 0.026 cm to about 1.0 cm, usually from about 0.251 cm to about 0.75 cm and more usually from about 0.3 cm to about 0.8 cm and the depth or thickness of slot 22 will typically range from about 128 µm to about 2400 µm.

Figure 7:
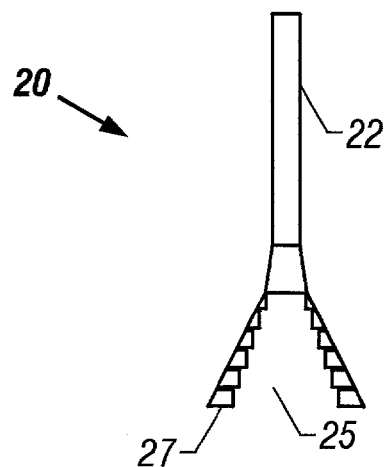
FIG. 7 shows a cross section of a subject test strip selecting element having a series of steps according to the subject invention.

In certain embodiments of the subject invention, the interior of the test strip selecting element 20 further includes a test strip directing element 27, i.e., the interior of the funnel-like cavity 25 includes a structure for directing at least one test strip therethrough. For example, a series of bumps or protrusions, studs, ribs steps, ridges, ledges or the like may be positioned on the interior of the test strip selecting element 20 to direct the test strip(s) towards the slot 22 and assist in separating a single test strip from others. The directing element 27 may be positioned in any suitable manner. For example, a series of ridges or steps may encircle the entire interior of the test strip selecting element 20 or may be positioned on a portion of the interior such as on two opposing sides of the test strip selecting element 20. Opposing steps may be offset in such a manner that the top of one step corresponds with the rise of an opposing step. FIG. 7 shows a cross sectional view through an exemplary test strip selecting element, such as a cross section taken along line x—x of test strip selecting element 20 of FIG. 5 having test strip 30a removed from test strip selecting element 25 to provide a better view of directing element 27. FIG. 7 shows test strip selecting element 20 having a series of steps or ridges 27 positioned at least on two opposing sides of the interior of the test strip selecting element 20.

Test Strip Holding Means

As described above, the subject invention also includes at least one test strip holding means for holding a test strip in a fixed position relative to cover 6, for example once the test strip has been selected by a test strip selecting element. In one embodiment, the test strip holding means includes a cover that has resiliently deformable walls (see FIG. 11). In another embodiment, the test strip holding means includes a test strip holding mechanism that is gravity controlled (see FIG. 8A). The test strip holding means will be further described herein with reference to holding a test strip 30a selected by a test strip selecting element 20, as described above. However, it is understood that this description is by way of example only and is in no way intended to limit the scope of the invention. That is, the test strip holding means may be used to hold any test strip placed in a suitable position using any convenient means. Each of the above-described test strip holding means will now be described in turn.

Resiliently Deformable Cover

Figure 11:
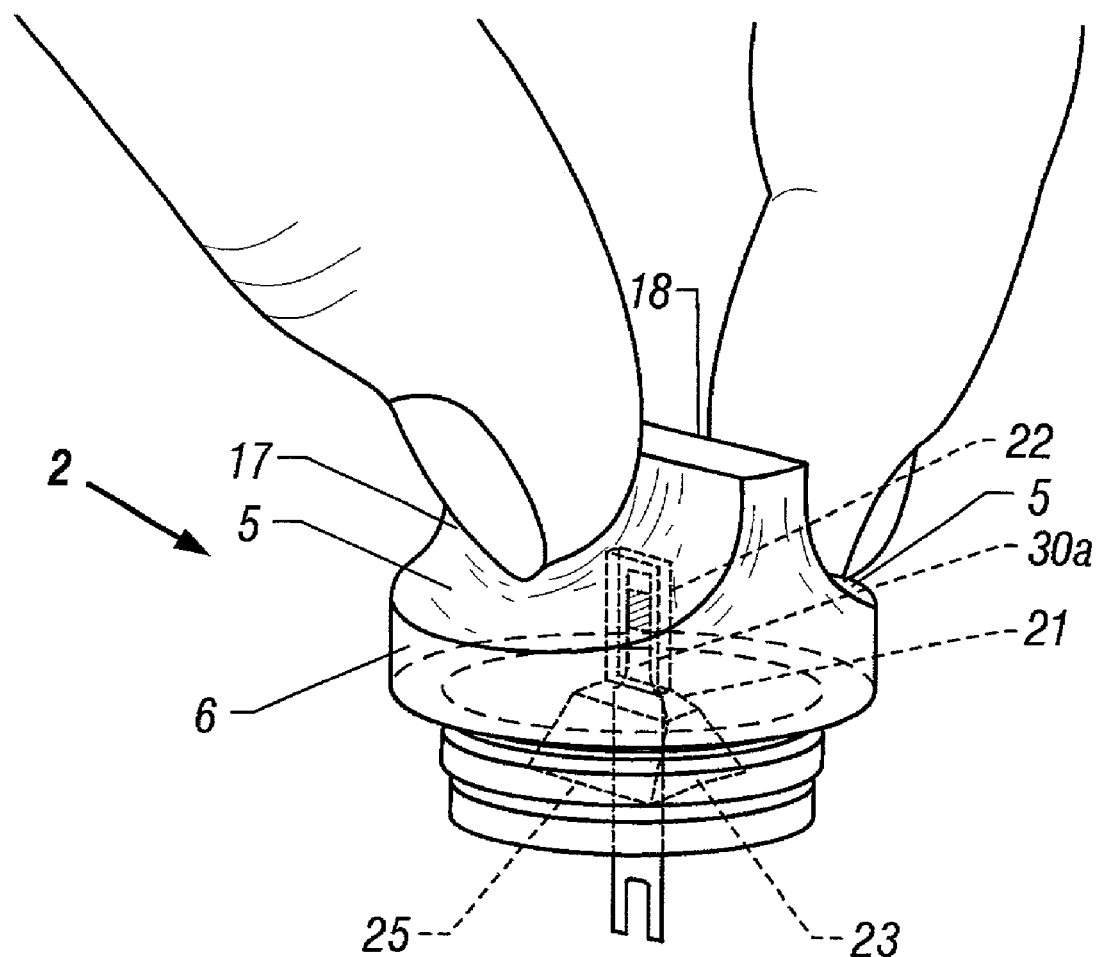
FIG. 11 shows an exemplary embodiment of a subject cover having resiliently deformable walls.

As mentioned above, certain embodiments of the subject devices include a test strip holding means that is made of a cover that has resiliently deformable walls. FIG. 11 shows an exemplary embodiment of cover 6 having resiliently deformable walls 17 and 18. By deformable is meant that one or more walls of a cover, typically at least two opposing walls, are capable of being urged inwardly or squeezed together upon application of a suitable force thereto. By resiliently deformable is meant that the deformation is not permanent and the walls are capable of resuming their original configuration upon release of force thereto. Any and all embodiments of the subject covers described herein may include one or more walls that are capable of resiliently deforming, such as walls 17 and 18 shown in FIG. 11 that include indents 5.

Accordingly, at least two opposing walls of a resiliently deformable cover 6 are made of a material that is resiliently deformable upon application of a slight force by an individual thereto, such as those materials described above.

The at least two opposing walls 17 and 18 are capable of deforming to such an extent that a test strip may be held in a fixed position therebetween. That is, at least two opposing walls are capable of being squeezed together to hold or pinch a test strip between them.

Test Strip Holding Mechanism

Figure 8A:
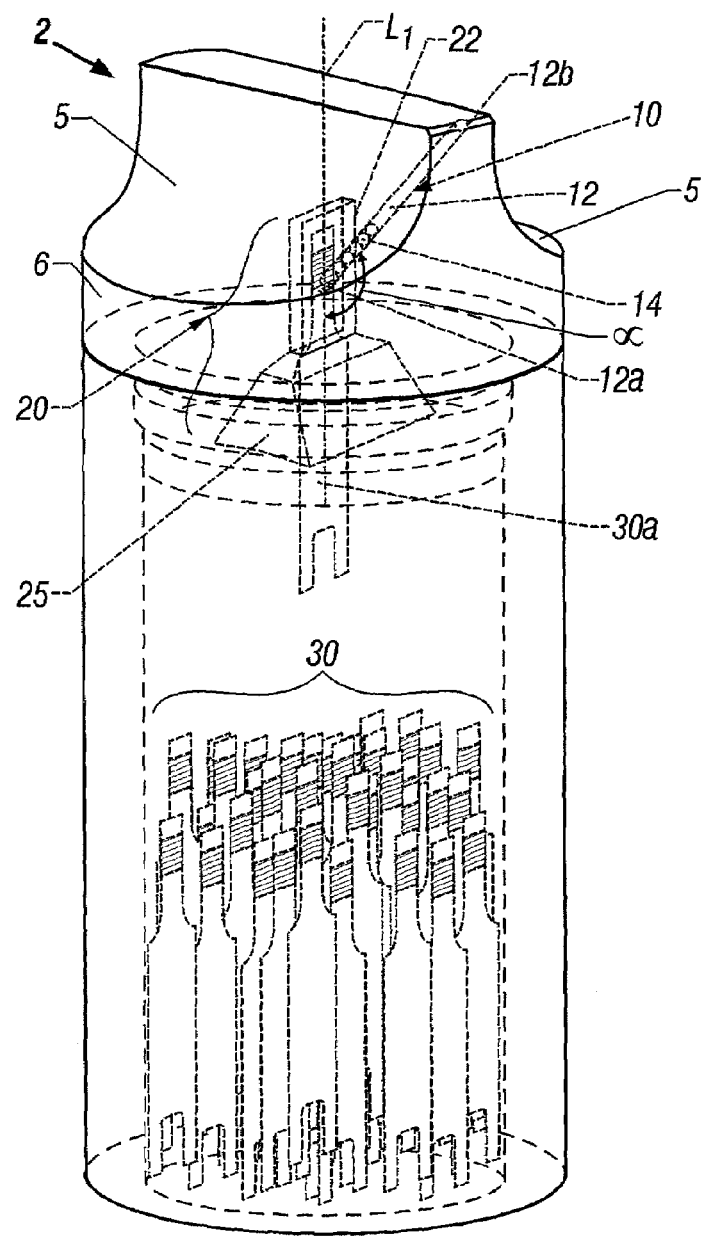
FIG. 8A shows a perspective view of a subject test strip container having a subject gravity controlled test strip holding mechanism.
Figure 8B:
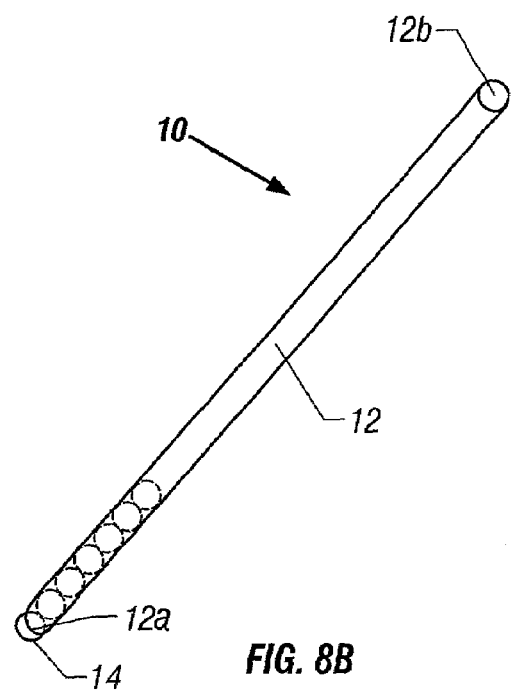
FIG. 8B shows an enlarged view of the gravity-controlled test strip holding mechanism of FIG. 4A.

As mentioned above, certain embodiments of the subject devices include a test strip holding means that includes a gravity controlled test strip holding mechanism. As shown in FIG. 8A, test strip holding mechanism 10 includes a channel 12 positioned adjacent slot 22 of test strip selecting element 20, wherein at least one slideable contact element 14 is disposed within channel 12. FIG. 8B shows an enlarged view of the test strip holding mechanism 10 of FIG. 8A. Channel 12 includes an open proximal end 12a and a distal end 12b, where distal end 12b may be opened or closed. As shown, when a contact element 14 is positioned adjacent open proximal end 12a of channel 12, contact element 14 slightly protrudes therefrom, i.e., a portion of contact element 14 extends from channel 12. In this manner, the slightly protruding contact element 14 may directly contact a test strip, such as test strip 30a that has been selected by slot 22 of test strip selecting element 20. In those embodiments employing a plurality of contact elements 14, the number of contact elements 14 within channel 12 may vary, but will typically range from about 1 to about 20, usually from about 1 to about 10 and more usually from about 1 to about 4, however a greater or fewer number of contact elements 14 may be present.

Test strip holding mechanism 10 is gravity controlled in that the contacting element(s) 14 are caused to engage or contact a test strip 30a when gravitational forces urge them against test strip 30a that is positioned in slot 22, which test strip 30a was once contained in base 4, i.e., when the device is handled such that the contact element(s) 14 slideably move adjacent proximal end 12a, as shown in FIGS. 8A and 8B and as will be described in more detail below. Accordingly, test strip holding mechanism 10 is gravity-controlled wherein gravitational forces cause the one or more contact elements 14 to slide or move within channel 12 when container 2 is moved to a substantially upright position, as described above, where such contact element(s) 14 are thus caused to contact a selected test strip 30a and hold it in a fixed position relative to cover 6.

Accordingly, channel 12 of the gravity-controlled test strip holding mechanism is positioned at an angle within cover 6 such that contact element(s) 14 therein are capable of slideably moving within channel 12 when cover 6 is positioned appropriately. That is, the test strip holding mechanism 10 defines an obtuse angle α relative to the longitudinal axis $L_1$ of the cover 6, as shown in FIG. 8A. That is, the angle α is such that when the container 2 is substantially upright, as shown in FIG. 8A, gravity forces act upon the contact element(s) 14 therein to slideably move the contact element(s) 14 in a direction towards open proximal end 12a of channel 12. As such, angle α will vary according to a variety of factors, including, but not limited to, the size, shape, weight and material(s) of construction of the contact element(s) 14, etc. Typically, angle α of the channel 12 ranges from about 120° to about 170° and more typically ranges from about 135° to about 150° relative to the longitudinal axis $L_1$ of cover 6.

The shape of the one or more contact elements 14 is not critical to the subject invention, where the shape thereof may include, but is not limited to, spherical such as spherical ball bearings, rod-like, tubular, round, disc, square, spherical, oblong, plate, cylindrical, etc., as long as the contact element(s) 14 are capable of sliding or moving within channel 12.

The size of the contact element(s) 14 will vary depending on a variety of factors, including, but not limited to, the size and shape of the test strip to be held thereby, the size of the cover, the materials of construction, etc. By way of example and not limitations, in certain embodiments 5 spherical contact elements 14 are used to hold a test strip 30a that has a length ranging from about 0.64 cm to about 7.6 cm, a width ranging from about 0.25 cm to about 0.76 cm and a thickness ranging from about 127 µm to about 1270 µm. As such, the diameter of each spherical contact element 14 typically ranges from about 0.025 cm to about 0.76 cm, usually from about 0.1 cm to about 0.67 cm and more usually from about 0.2 cm to about 0.4 cm, where the weight of each contact member typically ranges from about $7 \times 10^{-5}$ grams to about 1.8 grams, usually from about 0.004 grams to about 1.27 grams and more usually from about 0.033 grams to about 0.263 grams.

A feature of test strip holding mechanism 10 is that the contact element(s) 14 is configured to engage test strip 30a selected by slot 22 of test strip selecting element 20 and hold it in a fixed position in slot 22 simply by handling or manipulating container 2 to position it in an appropriate orientation relative to the ground, i.e., test strip holding mechanism 10 is passively activated to engage and hold a test strip 30a. Specifically, test strip holding mechanism 10 is gravity controlled, as described above, such that handling container 2 in a certain manner, i.e., positioning container 2 in a substantially upright orientation, causes gravitational forces to act upon contact element(s) 14 to cause contact element(s) 14 to engage and hold a test strip 30a selected by the test strip selecting element 20.

Systems

The above described devices may find use with systems that include the devices of the subject invention and at least an automated meter, such as of the type described above, for determining the concentration of an analyte in a sample and one or more test strips.

Methods

Also provided by the subject invention are methods for selecting a single test strip. More specifically, methods are provided that enable a single test strip to be easily selected so that it may be used, for example by a visually and/or dextrally impaired individual. According to the subject methods, a subject test strip container is provided and handled or positioned in a manner to cause the test strip(s) to move into the cover of the device where a single test strip is selected, usually from amongst a plurality of test strips. In certain embodiments, the subject methods also include holding a test strip in the cover such as a selected test strip, e.g., by resiliently deforming one or more walls of the cover and/or simply handling or positioning the container in a manner that causes a single test strip to be held in the cover of the device. Accordingly, the subject methods advantageously enable a single test strip to be selected for use by simply handling or positioning the subject device is a certain manner and also allow for a test strip such as a selected test strip to be held in a fixed position, also just by squeezing one or more walls of the cover and/or handling or positioning the container in a particular orientation relative to the ground.

As such, the first step is to provide a test strip container, where such a container is configured to store at least one test strip and more likely a plurality of test strips therein, such as the test strip container 2 described above having a base 4 with a plurality of test strips 30 retained therein and a cover 6. The cover may include one or both of a test strip selecting element 20 and a test strip holding means, e.g., at least one resiliently deformable wall and/or a test strip holding mechanism that is gravity controlled.

Figure 9A:
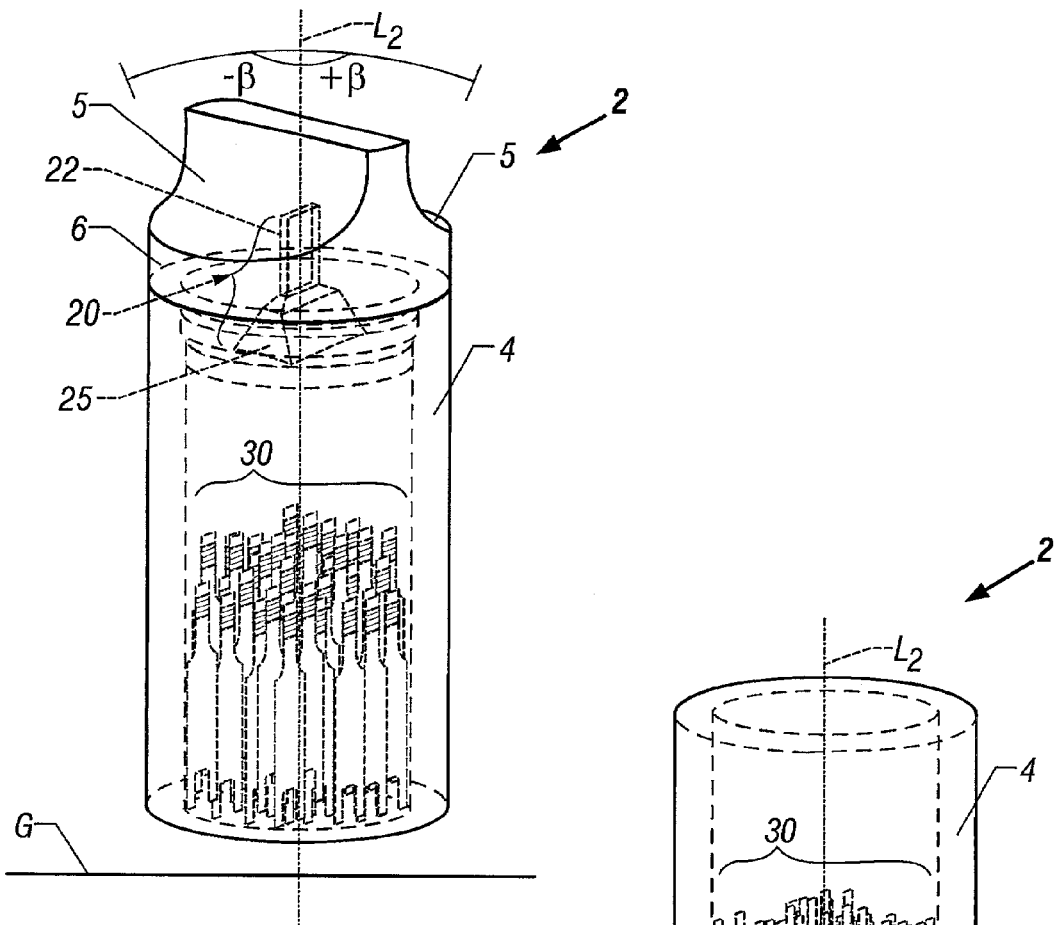
FIG. 9A shows an exemplary device according to the subject invention in a substantially upright position.
Figure 9B:
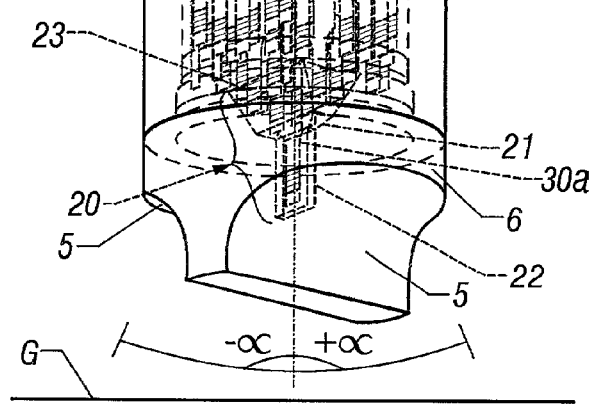
FIG. 9B shows an exemplary device according to the subject invention in a substantially upside down position.

Once the provision of a suitable container 2 is met, and at least one test strip is contained therein, the container 2 is positioned in a manner to cause the test strips 30 contained in base 4 thereof to move into cover 6. That is, container 2 is positioned so that it is substantially upside down. FIGS. 9A and 9B show container 2 in a substantially upright position and in a substantiality upside down position, respectively. By substantially upright is meant container 2 is at an angle β that ranges from about −30 to about +30 relative to the longitudinal axis $L_2$ of container 2 when the longitudinal axis $L_2$ of the container 2 is positioned perpendicular to the ground G and base 4 is closer to ground G than cover 6 is positioned with respect to the ground G. By substantially upside down is meant container 2 is at an angle γ that ranges from about −20 to about +20 relative to the longitudinal axis $L_2$ of the container 2 when the longitudinal axis $L_2$ of the container 2 is positioned perpendicular to the ground G and cover 6 is closer to the ground G than base 4 is positioned with repsect to the ground G.

Figure 10A:
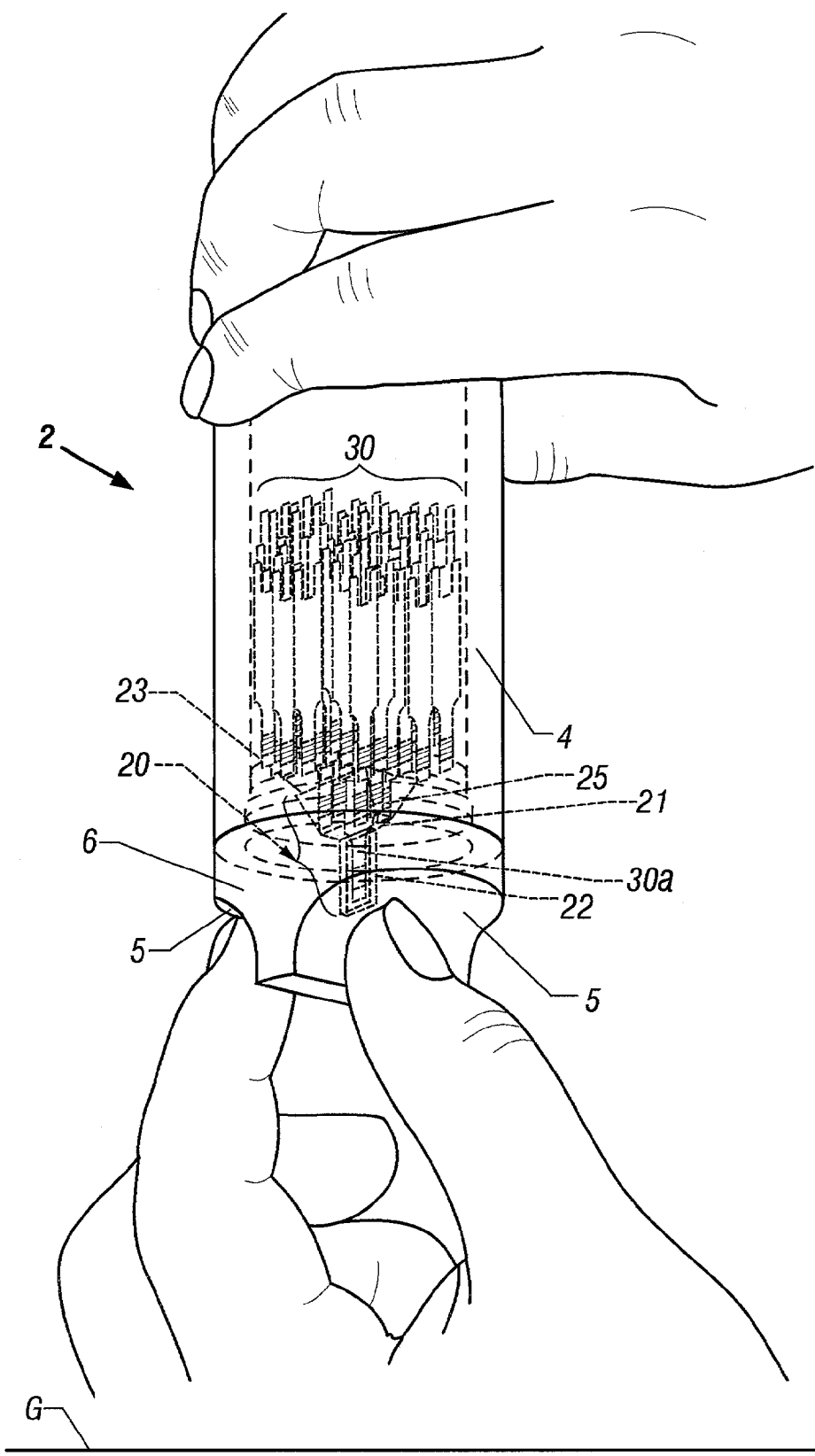
FIGS. 10A–10G illustrate the steps of the subject methods accordingly.
Figure 10B:
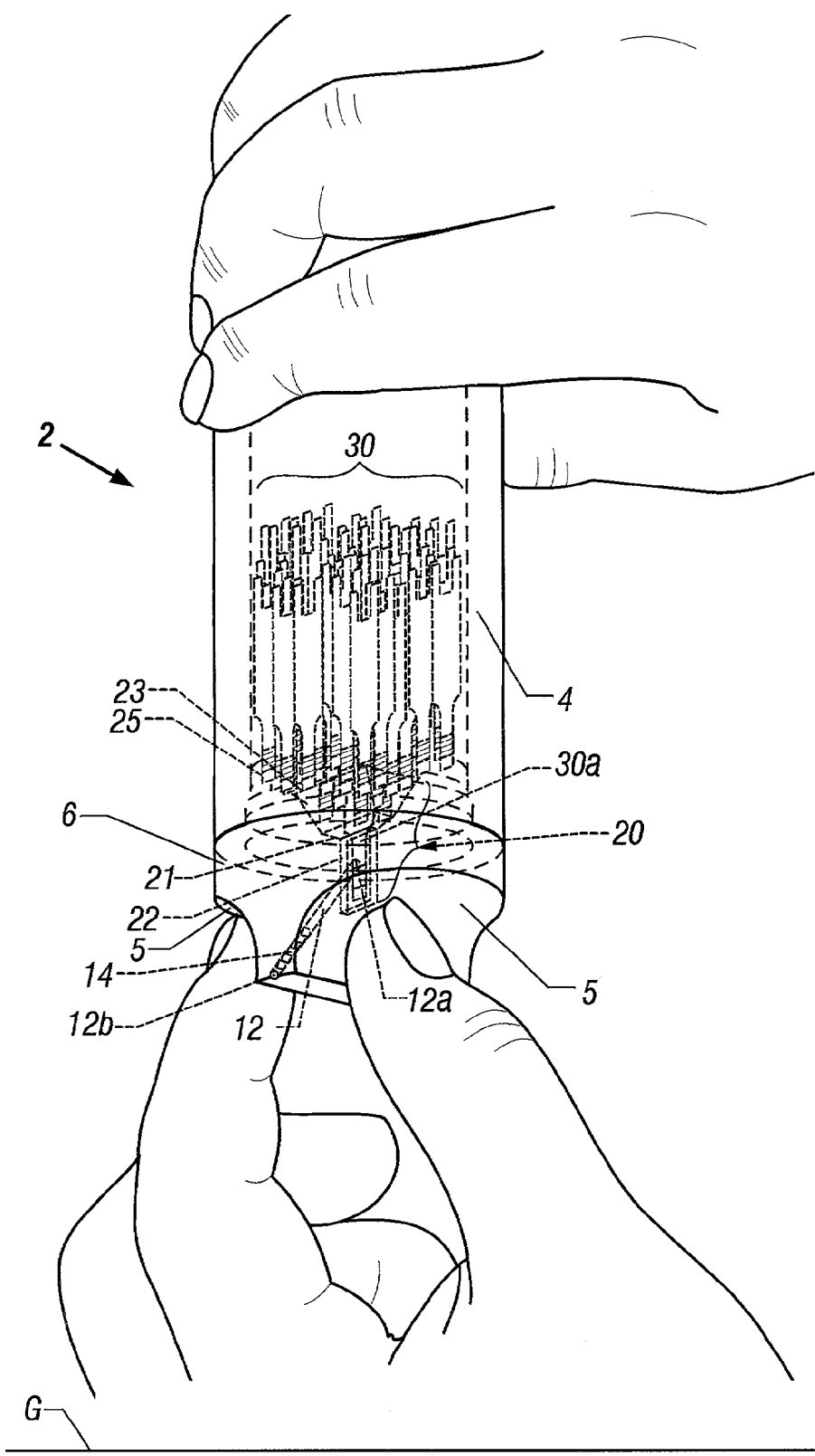

Referring to FIGS. 10A–10G which illustrate the steps of the subject methods in more detail, FIG. 10A illustrates container 2 being manually grasped and positioned in a substantially upside down position such that the test strips 30 contained in base 4 are moved into cover 6 when container 2 is in a substantially upside down position. Accordingly, if container 2 is originally in a substantially upright position, container 2 is turned or rotated such that it is in a substantially upside down position. As illustrated in FIG. 10B, if container 2 includes a test strip holding mechanism 10, in this substantially upside down position contact element(s) 14 are positioned towards distal end 12b of channel 12, i.e., away from proximal opening 12a of channel 12.

Furthermore, when container 2 is positioned in this manner, i.e., positioned substantially upside down, a single test strip 30a is selected or separated from the rest of the test strips 30. More specifically, the test strips 30 move into test strip selecting element 20 from base 4, which test strips 30 are then segregated by the continuously reduced diameter of the test strip selecting element 20, e.g., by a directing element 27 in certain instances. A single test strip 30a is ultimately segregated from the plurality 30 and selected by slot 22 so that at least a portion of the test strip 30a is positioned extending from slot 22 and a portion is positioned within slot 22 and within cavity 25, as shown in FIGS. 10A and 10B.

More specifically, a plurality of test strips 30 is moved from base 4 into second end 23 of continuously reduced diameter cavity 25 when the container 2 is positioned in a manner which causes the test strips 30 to move towards cover 6 and, as the test strips 30 move towards first end 21, the number of test strips gradually decreases due to the funnel-like portion or the tapered walls (and also due to a directing element if present) of cavity 25 of test strip selecting element 20. Ultimately, a single test strip 30a is separated from the remaining test strips 30 due to the funnel portion of test strip selecting element 20 and is selected by slot 22. In certain embodiments, the container 2 is gently agitated along the plane defined by −γ to +γ (see FIG. 9B) to facilitate test strip selection.

Figure 10C:
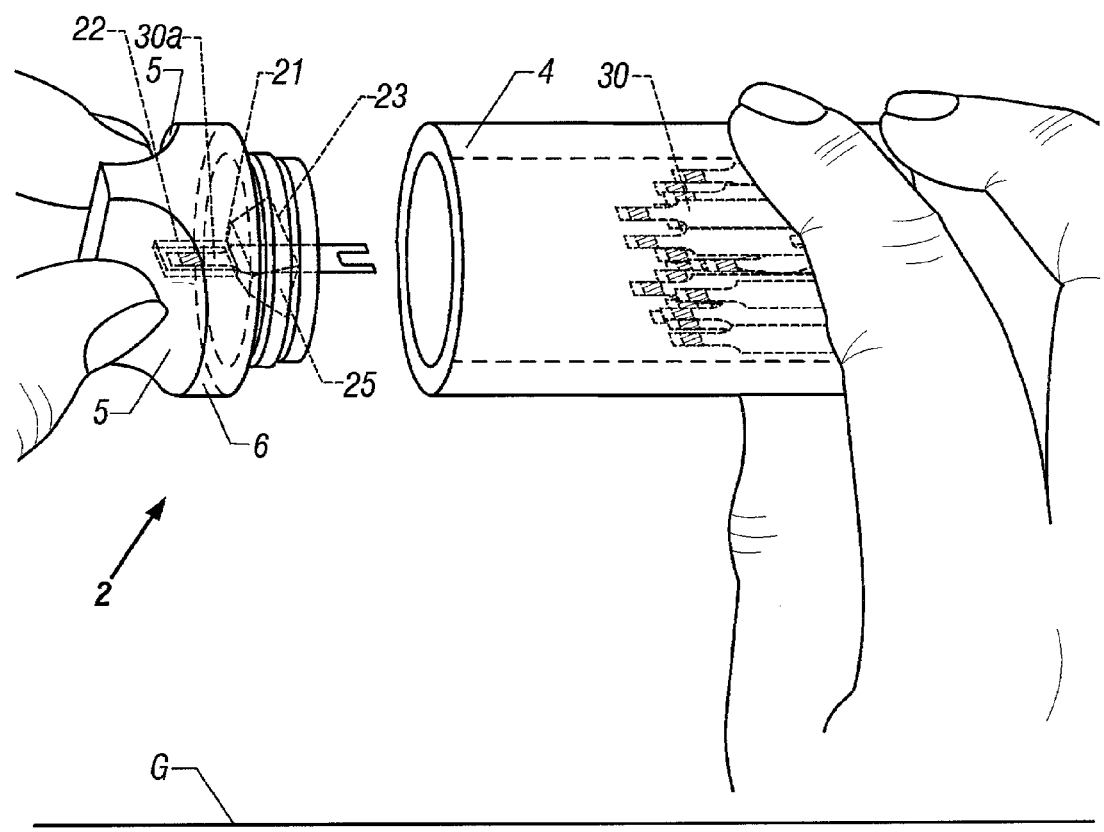

Once a single test strip 30a is selected within slot 22 of test strip selecting element 20, an individual simply handles the container 2 in an appropriate manner so that the selected test strip 30a may be used. In one embodiment of the subject methods, e.g., if a test strip holding means is not present, the container 2 is simply positioned in a substantially horizontal position relative to the ground (the longitudinal axis $L_2$ of the device is positioned substantially parallel relative to the ground G) to such an extent to cause the plurality of test strips 30 to move back into base 4 while the selected test strip 30a is retained in slot 22 of test strip selecting element 20 as illustrated in FIG. 10C. Base 4 is separated from cover 6 so as to provide access to the selected test strip 30a.

In certain other embodiment of the subject methods, the selected test strip 30a may be held in a fixed position in slot 22 using a test strip holding means, as described above. That is, a selected test strip 30a may be held in a fixed position in slot 22 by resiliently deforming one or more walls of cover 6 and/or by a test strip holding mechanism 10 that is gravity controlled.

Figure 10D:
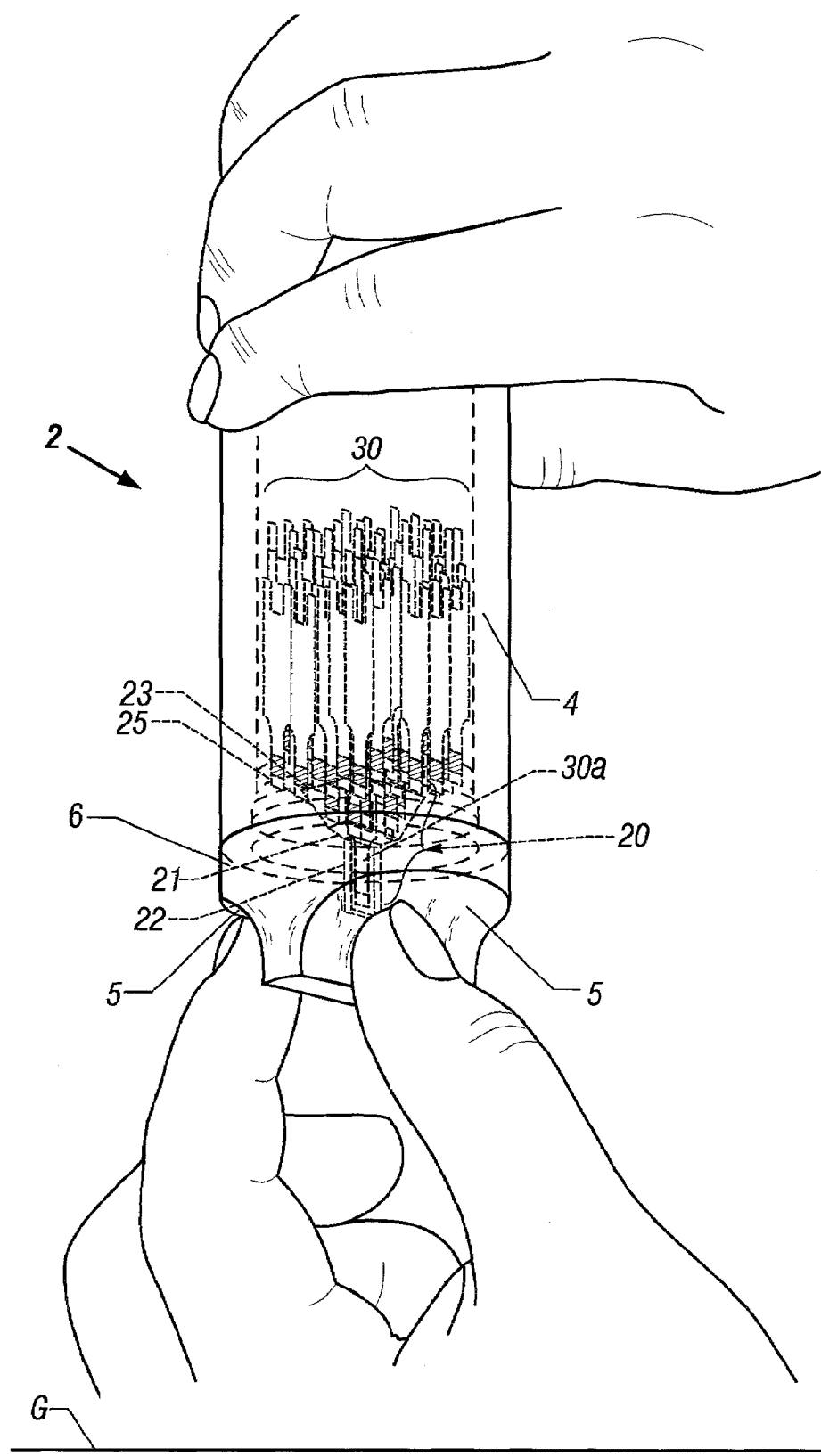

In those embodiments that hold a test strip by resiliently deforming one or more walls of the cover 6, one or more walls, typically two opposing walls, are engaged and resiliently deformed by urging them towards one another to hold a test strip 30a therebetween, as illustrated in FIG. 10D, and container 2 is positioned so that the plurality of test strips 30 is moved back into base 4 (positioned in a substantially horizontal or substantially upright position relative to the ground), where the order of the steps may be reversed as will be apparent. For example, as illustrated in FIG. 10D, an individual may grasp the resiliently deformable walls 17 and 18 at indents 5 of the cover 6 and apply a force thereto to urge resiliently deformable walls 17 and 18 together to an extent that they hold or pinch a test strip 30a between them. The force required to resiliently deform the walls to an extant so as to hold a test strip therebetween will vary depending on a variety of factors such as the material of construction of the walls, the dimensions of the test strip, etc. However, the force required will be minimal or slight to enable a dextrally impaired individual to easily use the device.

Figure 10E:
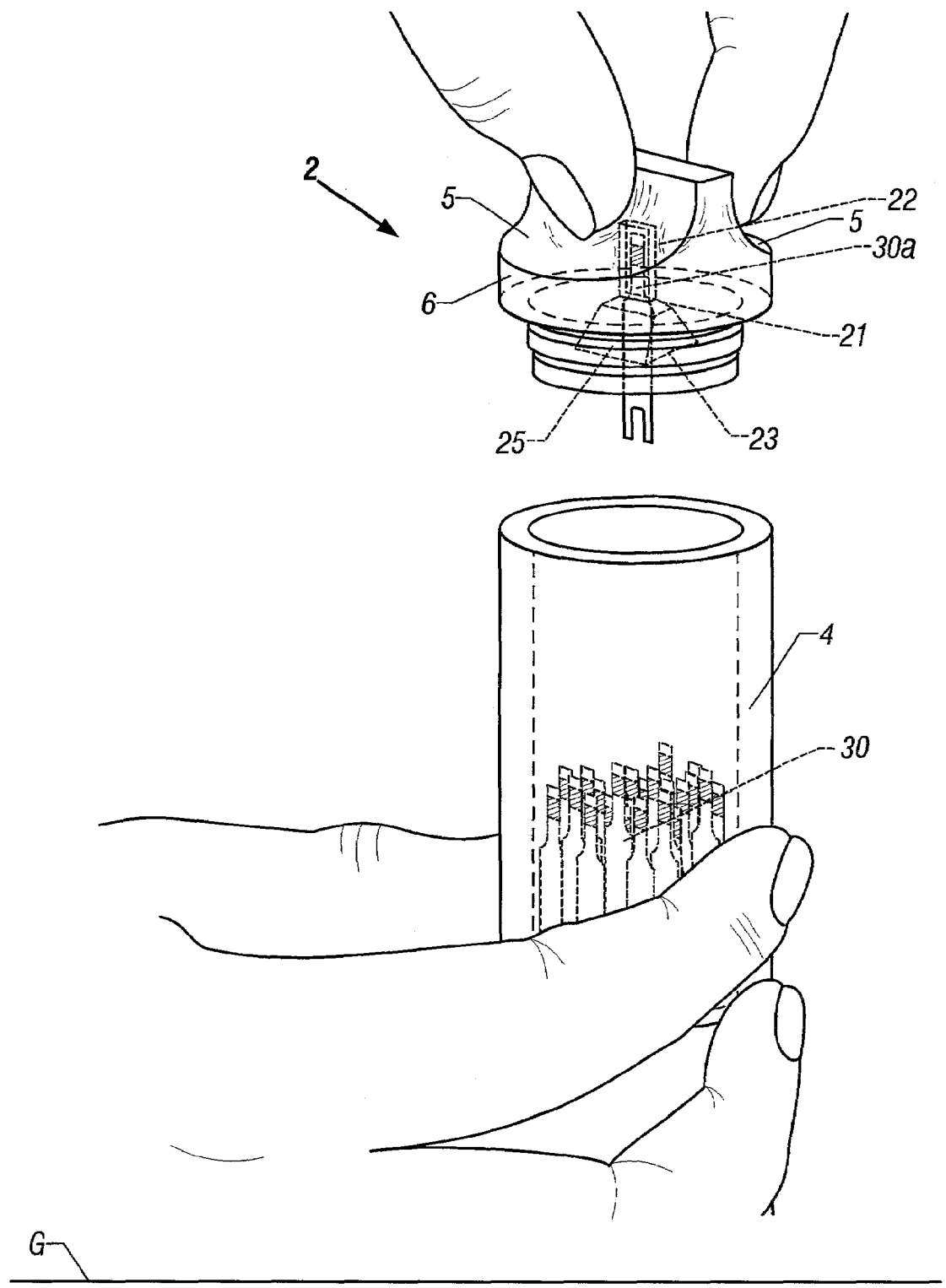

As illustrated in FIG. 10E, once the test strip 30a is held in a fixed position by the resiliently deformed walls 17 and 18 of cover 6, cover 6 is removed or separated from base 4 such that the test strip 30a is held in cover 6 and access is provided thereto. As illustrated in FIG. 10E, with a force applied to the walls 17 and 18 of cover 6 to resiliently deform them, test strip 30a is held in the cover 6 between the deformed walls 17 and 18 such that a portion of test strip 30a extends from slot 22 and a portion is positioned within slot 22 and more specifically within frustum-shaped cavity 25 of test strip selecting element 20. Typically, the portion that extends within cavity 25 is the area of the test strip 30a that provides contact with a meter. As such, an individual may choose to leave the test strip 30a inside cover 6 by continuing to apply a force to the cover 6 so that the test strip 30a is held in place by the resiliently deformed walls 17 and 18, such that cover 6 serves as a handle or grip for test strip 30a while the tests trip is associated with a meter. In this manner, an individual does not have to touch the test strip 30a or try to manipulate it while mating it with a meter and during subsequent sample application. In those embodiments where sample may be applied to a test strip prior to the test strip being associated with a meter, depending on the particular type and configuration of the test strip, the portion of the test strip extending within cavity 25 may be the portion of the test strip where sample is applied so that a user need not remove the test strip from the cover in order to apply sample thereto and the cover may be used as a handle or grip in this instance as well.

Alternatively or in addition to the above, an individual may choose to remove the test strip 30a from the cover 6 anytime after cover 6 has been separated from base 4, i.e., before or after association with a meter, by simply grasping the test strip 30a from cover 6, such as by the edges of the test strip 30a, e.g., with fingers, tweezers and the like, and/or terminating the pressure applied to the resiliently deformed walls. Accordingly, the force applied to the walls 17 and 18 of the cover 6 to resiliently deform them is terminated so as to release the hold on the test strip 30a by the walls 17 and 18. The test strip 30a is then gently pulled or tugged to remove it from cover 6.

Figure 10F:
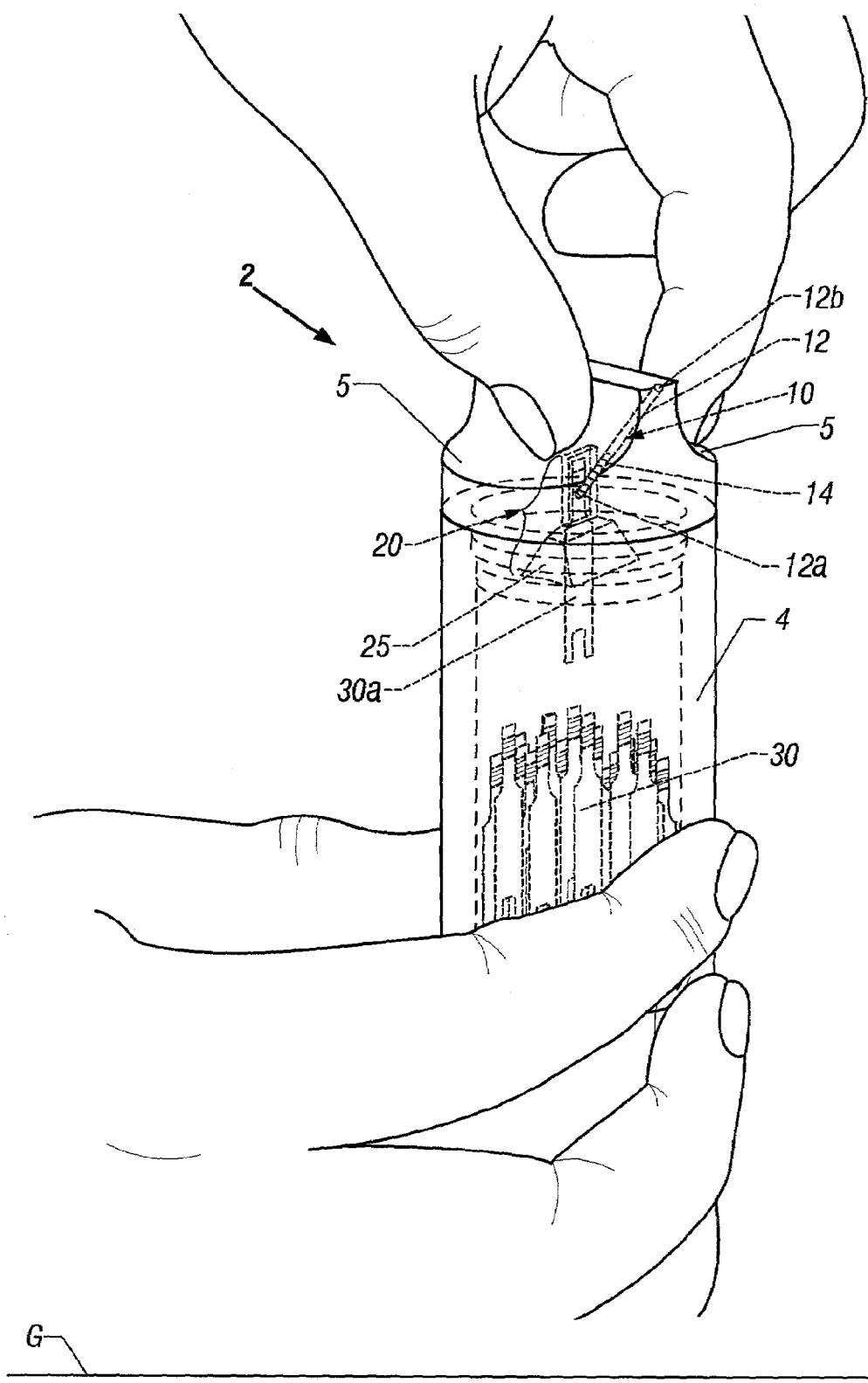

In those embodiments using a gravity controlled test strip holding mechanism 10 to hold a test strip in a fixed position relative to cover 6, in addition to or in place of a test strip holding means that includes resiliently deformed walls, container 2 is simply turned or rotated to a substantially upright position illustrated in FIG. 10F from the substantially upside down position illustrated in FIG. 10B. By handling the container 2 in such a manner, gravity slideably moves the one or more contact elements 14 in a direction towards open proximal end 12a of channel 12 such that they come to rest adjacent open end 12a. When positioned adjacent open end 12a, the most proximal contact element 14, i.e., the contact element 14 that is positioned directly against open end 12a, protrudes therefrom a suitable distance so as to engage test strip 30a in slot 22 thereby urging against test strip 30a with a force, causing the test strip 30a to be held in a fixed position within slot 22 between contact element 14 positioned in open end 12a and a wall of slot 22. The distance the contact element 14 will protrude will be a distance sufficient to hold a test strip in a fixed position, where that distance will vary depending on a variety of factors such as the size, shape and weight of contact element 14, the number of contact elements positioned in channel 12, the dimensions of channel 12, etc.

The force exerted by gravity-induced test strip holding mechanism 10 upon a portion of the test strip 30a to hold it in a fixed position in slot 22 will be a force sufficient to hold a test strip in a fixed position and will vary depending on a variety of factors such as the size of the test strip, the size, shape and weight and material of construction of the contact element(s) 14, and the like.

Figure 10G:
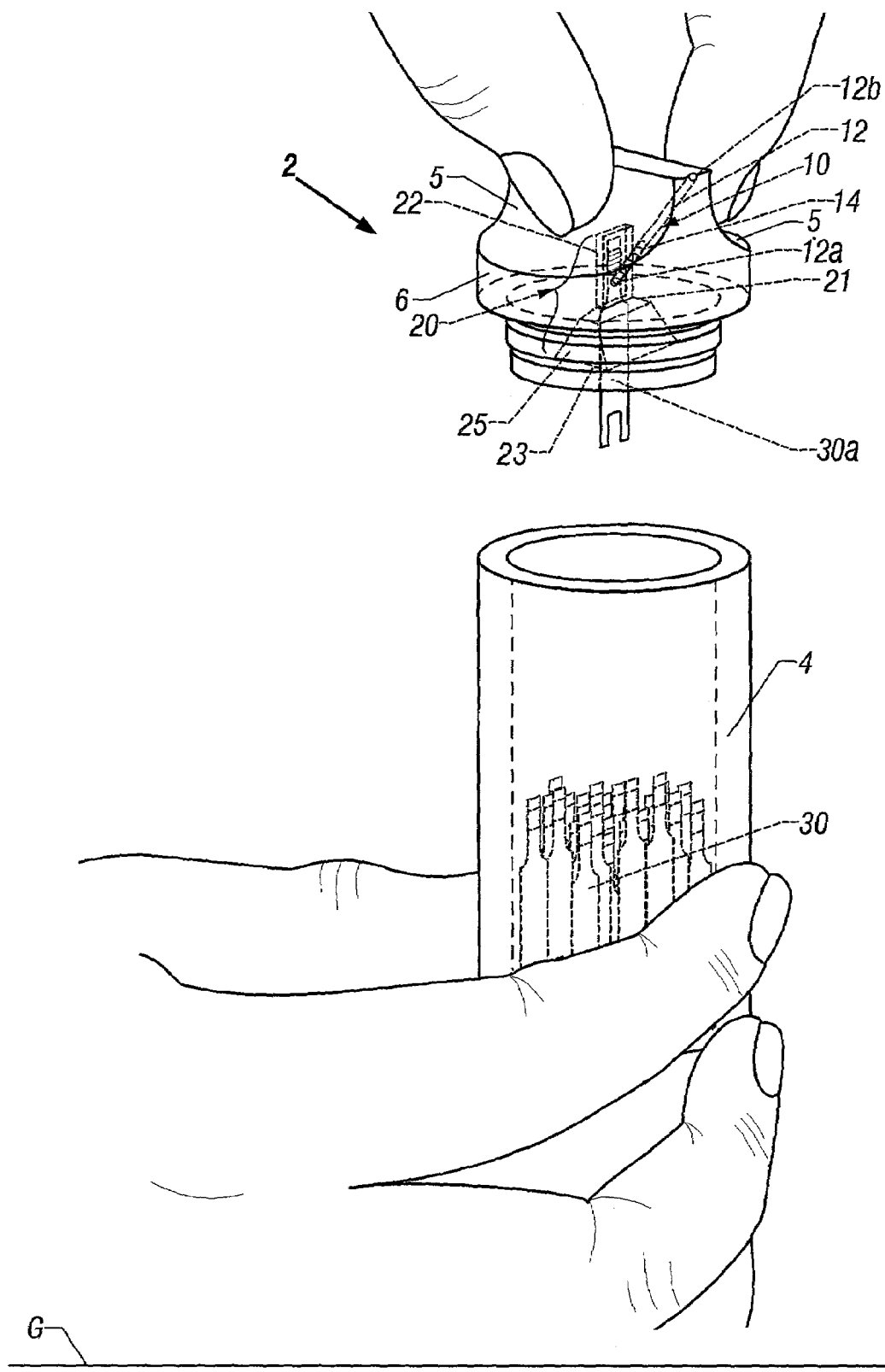

As illustrated in FIG. 10G, once the test strip 30a is held in a fixed position by gravity-controlled test strip holding mechanism 10, cover 6 is removed or separated from base 4 such that the test strip 30a is held in cover 6 and access is provided thereto. For instance, maintaining container 2 in a substantially upright position, an individual may grasp the indents 5 of the cover 6 and separate cover 6 from base 4. As illustrated in FIGS. 10F and 10G, with cover 6 in a substantially upright position, test strip 30a is held in cover 6, i.e., it is held by gravity-controlled test strip holding mechanism 10, such that a portion of test strip 30a is positioned in slot 22 and a portion is positioned within or extending from substantially frustum-shaped cavity 25 of test strip selecting element 20. Typically, the portion that extends within cavity 25 is the area of the test strip 30a that is contacted with a meter. As such, an individual may choose to leave the test strip 30a inside cover 6, held in place by gravity-controlled test strip holding mechanism 10, such that cover 6 serves as a handle or grip for test strip 30a. In this manner, an individual does not have to touch test strip 30a or try to manipulate it while it is mated with a meter and during subsequent sample application. In those embodiments where sample may be applied to a test strip prior to the test strip being associated with a meter, depending on the particular type and configuration of the test strip, the portion of the test strip extending within cavity 25 may be the portion of the test strip where sample is applied so that a user need not remove the test strip from the cover in order to apply sample thereto and the cover may be used as a handle or grip in this instance as well.

Alternatively or in addition to the above, an individual may choose to remove the test strip 30a from cover 6 anytime after cover 6 has been separated from base 4, i.e., before or after association with a meter, by simply grasping the test strip 30*a* from the substantially upright cover 6, such as by the edges of the test strip 30*a*, e.g., with fingers, tweezers and the like, and gently pulling or tugging the test strip 30*a* to disengage it from gravity-controlled test strip holding mechanism 10 and/or by slightly turning or rotating cover 6 to a position such that the contact members 14 slideably move away from the test strip 30*a*, at which time the test strip 30 may be easily removed from cover 6.

Kits

Finally, kits for practicing the subject methods are provided. The subject kits at least include one or more test strip dispensing devices of the subject invention. Oftentimes, a plurality of subject devices is included. The subject kits may also include one or more test strips, usually a plurality of test strips. The kits may further include a meter for automatically determining the presence and/or concentration of at least one analyte in a physiological sample applied to a test strip. The subject kits may further include an element for obtaining a physiological sample. For example, where the physiological sample is blood, the subject kits may further include an element for obtaining a blood sample, such as a lance for sticking a finger, a lance actuation means, and the like. In addition, the subject kits may include a calibration means for calibrating the instrument, e.g., a control solution or standard, e.g., a control solution that has a known analyte concentration such as a known glucose concentration. The kits may also include instructions for using the subject devices for dispensing test strips and may also include instruction for determining the presence and/or concentration of at least one analyte in a physiological sample applied to a test strip. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

It is evident from the above description and discussion that the above described invention provides a simple, quick and convenient way to dispense test strips. The above described invention provides a number of advantages, including, but not limited to, ease and low cost manufacture, minimal components, portability, ease of use, particularly for visually and dextrally impaired individuals, and minimal test strip damage from contaminants from an individual's hands. As such, the subject invention represents a significant contribution to the art.

The subject invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

The specific devices and methods disclosed are considered to be illustrative and not restrictive. Modifications that come within the meaning and range of equivalents of the disclosed concepts, such as those that would readily occur to one skilled in the relevant art, are intended to be included within the scope of the appended claims.

What is claimed is:

1. A device for containing at least one test strip and dispensing a single test strip at a time, said device comprising:
   (a) a base capable of containing at least one test strip; and
   (b) a cover separable from the base and comprising a test strip selecting element having a continuously reduced cross-sectional area and means for selecting and holding a test strip in a fixed position relative to the cover so that a test strip positioned in the base can be gripped by the cover and removed from the base when the cover is separated from the base.

2. The device according to claim 1, wherein said continuously reduced cross-sectional area is a substantially frustum shaped cavity.

3. The device according to claim 2, wherein said substantially frustum-shaped cavity has a circular cross section, elliptical cross section or a rectangular cross section.

4. The device according to claim 1, wherein said test strip selecting element comprises a test strip selecting slot.

5. The device according to claim 4, wherein said test strip selecting slot is configured to be permissive of only a single test strip at a time.

6. The device according to claim 1, wherein said test strip selecting element further comprises a directing element for directing said single test strip through said test strip selecting element.

7. The device according to claim 6, wherein said directing element comprises a series of steps.

8. The device according to claim 2, wherein at least a portion of said cover comprises resiliently deformable walls.

9. The device according to claim 1, further comprising a gravity controlled test strip holding mechanism wherein said mechanism is subject to gravitational forces when said device is in a substantially upright position.

10. The device according to claim 9, wherein said gravity controlled test strip holding mechanism comprises a channel and at least one test strip contact element disposed within said channel.

11. The device according to claim 10, wherein said at least one test strip contact element is selected from the group consisting of one or more spherical balls and one or more rods.

12. The device according to claim 10, wherein said channel is positioned at an angle sufficient for gravity to slideably move said at least one test strip contact element within said channel when said device is appropriately positioned.

13. The device according to claim 12, wherein said angle ranges from about 120° to about 170° relative to the longitudinal axis of said cover.

14. A device for containing at least one test strip and dispensing a single test strip at a time, said device comprising:
   (a) a base capable of containing at least one test strip; and
   (b) a cover separable from the base and comprising a test strip selecting element and a gravity-controlled test strip holding mechanism operatively associated with the test strip selecting element wherein said mechanism is subject to gravitational forces that cause said mechanism to hold a test strip in a fixed position relative to the cover when said device is in a substantially upright position so that a test strip positioned in the base can be gripped by the cover and removed from the base when the cover is separated from the base.

15. The device according to claim 14, wherein said test strip selecting element comprises a continuously reduced cross-sectional area.

16. The device according to claim 14, wherein said continuously reduced cross-sectional area is a substantially frustum-shaped cavity.

17. The device according to claim 16, wherein said substantially frustum-shaped cavity has a circular cross section, a rectangular cross-section or an elliptical cross-section.

18. The device according to claim 14, wherein said test strip selecting element comprises a test strip selecting slot.

19. The device according to claim 18, wherein said test strip selecting slot is configured to be permissive of only a single test strip at a time.

20. The device according to claim 14, wherein said test strip selecting element further comprises a directing element for directing said single test strip through said test strip selecting element.

21. The device according to claim 20, wherein said directing element comprises a series of steps.

22. The device according to claim 14, wherein said gravity controlled test strip holding mechanism comprises a channel and at least one test strip contact element disposed within said channel.

23. The device according to claim 22, wherein said at least one test strip contact element is selected from the group consisting of one or more spherical balls and one or more rods.

24. The device according to claim 22, wherein said channel is positioned at an angle sufficient for gravity to slideably move said at least one test strip contact element within said channel when said device is appropriately positioned.

25. The device according to claim 24, wherein said angle ranges from about 120° to about 170° relative to the longitudinal axis of said cover.

26. The device according to claim 14, further comprising a test strip holding means.

27. The device according to claim 26, wherein said test strip holding means comprises resiliently deformable walls.

28. The device according to claim 26, wherein said test strip holding means comprises a gravity controlled test strip holding mechanism.

29. A device for containing at least one test strip and dispensing a single test strip at a time, said device comprising:
(a) a base; and
(b) a cover, wherein said cover has resiliently deformable walls that deform to hold a test strip in a fixed position.

30. The device according to claim 29, further comprising a test strip selecting element.

31. The device according to claim 30, wherein said test strip selecting element comprises a test strip selecting slot.

32. The device according to claim 30, wherein said test strip selecting element further comprises a continuously reduced cross-sectional area.

33. The device according to claim 32, wherein said continuously reduced cross-sectional area is a substantially frustum-shaped cavity.

34. The device according to claim 33, wherein said substantially frustum-shaped cavity has a circular cross section, a rectangular cross section or an elliptical cross-section.

35. The device according to claim 30, wherein said test strip selecting element further comprises a directing element.

36. The device according to claim 35, wherein said directing element comprises a series of steps.

37. The device according to claim 29, further comprising a gravity controlled test strip holding mechanism wherein said mechanism is subject to gravitational forces when said device is in a substantially upright position.

38. The device according to claim 37, wherein said gravity controlled test strip holding mechanism comprises a channel and at least one test strip contact element disposed within said channel.

39. The device according to claim 38, wherein said at least one test strip contact element is selected from the group consisting of one or more spherical balls and one or more rods.

40. The device according to claim 38, wherein said channel is positioned at an angle sufficient for gravity to slideably move said at least one test strip contact element within said channel when said device is appropriately positioned.

41. The device according to claim 40, wherein said angle ranges from about 120° to about 170° relative to the longitudinal axis of said cover.

42. A method for containing at least one test strip and selecting a single test strip at a time, said method comprising:
(a) providing a device comprising a cover and a base containing at least one test strip therein; and
positioning said device with respect to the ground to cause said single test strip to move from said base to said cover, whereby said single test strip is selected within said cover.

43. The method according to claim 42, further comprising holding said selected test strip in a fixed position within said cover.

44. The method according to claim 43, wherein said holding comprises placing said device in a substantially upright position.

45. The method according to claim 44, wherein said substantially upright position comprises an angle that ranges from about −30° to about +30° relative to the longitudinal axis of said device when said device is positioned perpendicular to the ground and said base is closer to said ground than said cover is positioned with respect to said ground.

46. The method according to claim 43, wherein said holding is accomplished by resiliently deforming at least one wall of said cover.

47. The method according to claim 43, wherein said holding is accomplished by a gravity-controlled element, said element being subject to gravitational forces.

48. The method according to claim 42, wherein said step of positioning comprises placing said device in a substantially upside down position.

49. The method according to claim 48, wherein said substantially upside down position comprises an angle that ranges from about −20 to about +20 relative to the longitudinal axis of said device when said device is perpendicular to the ground and said cover is closer to said ground than said base is closer to said ground.

50. The method according to claim 42, wherein said cover further comprises a continuously reduced cross sectional area, and said step of positioning comprises moving said single test strip through said continuously reduced cross sectional area.

51. The method according to claim 42, further comprising separating said cover from said base, wherein said single test strip is in said cover.

52. The method according to claim 42, wherein a plurality of test strips is contained in said device.

53. The method according to claim 42, further comprising applying a sample to said selected test strip.

54. The method according to claim 53, further comprising determining the concentration of at least one analyte in said sample.

55. The method according to claim 54, further comprising inserting said selected test strip in a meter for automatically determining the concentration of said at least one analyte.

56. A method for containing at least one test strip and holding a single test strip at a time, said method comprising:
(a) providing a device comprising a cover and a base containing at least one test strip therein;
(b) positioning said device with respect to the ground to cause said single test strip to move from said base to said cover; and
(c) holding said single test strip in a fixed position in said cover with a test strip holding means.

57. The method according to claim 56, wherein said holding comprises placing said device in a substantially upright position.

58. The method according to claim 57, wherein said substantially upright position comprises an angle that ranges from about −30° to about +30° relative to the longitudinal axis of said device when said device is positioned perpendicular to the ground and said base is closer to said ground than said cover is positioned with respect to said ground.

59. The method according to claim 56, wherein said holding is accomplished by resiliently deforming at least one wall of said cover.

60. The method according to claim 56, wherein said step of positioning comprises placing said device in a substantially upside down position.

61. The method according to claim 60, wherein said substantially upside down position comprises an angle that ranges from about −20 to about +20 relative to the longitudinal axis of said device when said device is perpendicular to the ground and said cover is closer to said ground than said base is closer to said ground.

62. The method according to claim 56, wherein said holding is accomplished by a gravity-controlled test strip holding element, said element being subject to gravitational forces.

63. The method according to claim 56, further comprising, prior to holding said single test strip, selecting said single test strip in said cover.

64. The method according to claim 56, wherein said cover further comprises a substantially continuously reduced cross-sectional area, and said step of positioning comprises moving said single test strip through said continuously reduced cross sectional area.

65. The method according to claim 56, further comprising separating said cover from said base, wherein said single test strip is in said cover.

66. The method according to claim 56, wherein a plurality of test strips is contained in said device.

67. The method according to claim 56, further comprising applying a sample to said held test strip.

68. The method according to claim 67, further comprising determining the concentration of at least one analyte in said sample.

69. The method according to claim 68, further comprising inserting said held test strip in a meter for automatically determining the concentration of said at least one analyte.

70. A method for containing at least one test strip and selecting a single test strip at a time, said method comprising:
(a) providing a device comprising a test strip selecting element comprising a continuously reduced cross-sectional area, wherein said device contains at least one test strip therein; and
(b) positioning said device with respect to the ground to cause said single test strip to move through said continuously reduced cross-sectional area.

71. The method according to claim 70, wherein said continuously reduced cross-sectional area is a substantially frustum-shaped cavity.

72. A kit for containing at least one test strip and dispensing a single test strip at a time, said kit comprising:
(a) at least one device according to claim 1; and
(b) a substrate comprising instruction for using said at least one device.

73. The kit according to claim 72, further comprising at least one test strip.

74. The kit according to claim 73, wherein said test strips are electrochemical test strips.

75. The kit according to claim 73, wherein said test strips are colorimetric test strips.

* * * * *